(12) United States Patent
Ma

(10) Patent No.: US 11,051,843 B2
(45) Date of Patent: Jul. 6, 2021

(54) NEEDLE ARRAY GUIDE FOR SKIN GRAFT EXPANSION APPARATUS, SKIN GRAFT EXPANSION APPARATUS AND SKIN GRAFTING SYSTEM INCLUDING THE SAME, AND RELATED METHODS AND COMPONENTS

(71) Applicant: Bing Ma, Clarksburg, MD (US)

(72) Inventor: Bing Ma, Clarksburg, MD (US)

(*) Notice: Subject to any disclaimer, the term of this patent is extended or adjusted under 35 U.S.C. 154(b) by 304 days.

(21) Appl. No.: 16/125,207

(22) Filed: Sep. 7, 2018

(65) Prior Publication Data

US 2019/0090897 A1    Mar. 28, 2019

Related U.S. Application Data

(60) Provisional application No. 62/564,745, filed on Sep. 28, 2017.

(51) Int. Cl.
*A61B 17/322* (2006.01)
*A61L 27/36* (2006.01)
(Continued)

(52) U.S. Cl.
CPC ...... *A61B 17/322* (2013.01); *A61B 17/32053* (2013.01); *A61B 90/02* (2016.02); *A61L 27/362* (2013.01); *A61L 27/3691* (2013.01); *A61L 27/54* (2013.01); *A61L 27/60* (2013.01); *A61B 17/205* (2013.01); *A61B 2017/00761* (2013.01);
(Continued)

(58) Field of Classification Search
CPC ............ A61B 17/322; A61B 17/32053; A61B 17/0482; A61B 2017/3225; A61B 90/02; A61M 37/0015; A61M 2037/0023; A61M 2037/003; A61M 2037/0038;
(Continued)

(56) References Cited

U.S. PATENT DOCUMENTS 3,841,334 A * 10/1974 Wolf ............... A61M 5/008
                                                      128/207.29
2005/0137525 A1* 6/2005 Wang ............ A61M 37/0015
                                                      604/93.01
2014/0004159 A1    1/2014 Xie et al.

OTHER PUBLICATIONS

"*Tissue engineering of skin*"; Sophie Bottcher-Haberzeth et al.; Tissue Biology Research Unit; Department of Surgery, University Children's Hospital Zurich; Zurich Switzerland; Burns 36 (2010) 450-460; Aug. 14, 2009; (11 pages).

(Continued)

*Primary Examiner* — Majid Jamialahmadi

(74) *Attorney, Agent, or Firm* — Staas & Halsey LLP

(57) ABSTRACT

A needle array guide for a skin graft expansion apparatus includes: a lower side having openings; and guide channels respectively leading to the openings and converging closer toward one another as the guide channels approach the openings, the guide channels configured to receive a plurality of hollow needles, arranged in a needle array and having respective tips to be attachable to minced skin particles obtained from a skin graft, to thereby guide movement of the plurality of hollow needles when the plurality of hollow needles are being protruded from the openings toward the minced skin particles and when the plurality of hollow needles are being retracted toward the openings. The needle array guide may be included as part of a skin graft expansion apparatus that further comprises the needle array. The skin graft expansion apparatus may be included as part of a skin grafting system.

25 Claims, 12 Drawing Sheets

(51) Int. Cl.
 A61L 27/54 (2006.01)
 A61L 27/60 (2006.01)
 A61B 17/3205 (2006.01)
 A61B 90/00 (2016.01)
 A61L 27/38 (2006.01)
 A61B 17/20 (2006.01)
 A61B 17/00 (2006.01)
 A61B 17/30 (2006.01)
 A61B 17/34 (2006.01)

(52) U.S. Cl.
 CPC .............. A61B 2017/00969 (2013.01); A61B 2017/306 (2013.01); A61B 2017/3225 (2013.01); A61B 2017/3411 (2013.01); A61L 27/3804 (2013.01); A61L 2400/12 (2013.01); A61L 2430/40 (2013.01)

(58) Field of Classification Search
 CPC .. A61M 2037/0046; A61M 2037/0061; A61M 5/42; A61M 5/422; A61M 5/425
 See application file for complete search history.

(56) References Cited

OTHER PUBLICATIONS

"An Alternative Treatment Strategy for Complicated Chronic Wounds: Negative Pressure Therapy over Mesh Skin Graft"; Feb. 16, 2017; Michele Maruccia et al.; Hindawi Publishing Corporation BioMed Research International vol. 2017, Article ID 8395219, http://dx.doi.org/10.1155/2017/8395219 ; (7 pages).

"Postburn Head and Neck Reconstruction: An Algorithmic Approach"; Paul Immanuel Heidekrueger, MD et al.; The Journal of Craniofacial Surgery; vol. 27, No. 1, Jan. 2016 (6 pages).

"Serial Cultivation of Strains of Human Epidermal Keratinocytes: the Formation of Keratinizing Colonies from Single Cells"; James G. Rheinwald et al.; Department of Biology, Massachusetts Institute of Technology Cambridge, MA 02139; Cell, vol. 6, 331-344, Nov. 1975 (12 pages).

"Long-Term Regeneration of Human Epidermis on Third Degree Burns Transplanted with Autologous Cultured Epithelium Grown on a Fibrin Matrix"; Vincent Ronfard et al.; Transplantation 0041-1337/00/7011-1588/0; vol. 70, 1588-1598, No. 11, Dec. 15, 2000 (11 pages).

"Human Skin Basement Membrane in Health and in Autoimmune Diseases"; Lawrence S. Chan; Frontiers in Bioscience 2, d343-352, Jul. 15, 1997 (10 pages).

"Bioengineered skin substitutes for the management of burns: A systematic review"; Clarabelle Pham et al.; Burns 33 (2007) 946-957; Mar. 26, 2007 (12 pages).

"Burn Wounds Resurfaced by Cultured Epidermal Autografts Show Abnormal Reconstitution of Anchoring Fibrils"; David T. Woodley, MD, et al.; JAMA, May 6, 1988, vol. 259, No. 17; (6 pages).

"Cultural epithelial autograft (CEA) in burn treatment: Three decades later"; Bishara S. Atiyeh et al.; Burns 33 (2007) 405-413; Nov. 4, 2006; (9 pages).

"Skin grafting and wound healing-the "dermato-plastic team approach""; Robert Hierner, MD, PhD, et al.; Clinics in Dermatology (2005) 23, Jul. 28, 2004; 343-352; (10 pages).

"Excision and Skin Grafting of Thermal Burns"; Dennis P. Orgill, M.D., Ph.D.; New England Journal of Medicine; Feb. 26, 2009 (893-901); (9 pages).

"Artificial skin, split-thickness autograft and cultured autologous keratinocytes combined to treat a severe burn injury of 93% of TBSA"; M. Loss et al.; Burns 26 (2000) 644-652; Accepted Jan. 25, 2000 (9 pages).

"The Mesh Skin Graft"; James C. Tanner, Jr., et al.; Plastic and Reconstructive Surgery; vol. 34, No. 3; Copyright @ 1964; (6 pages).

"Fractional Skin Harvesting: Autologous Skin Grafting without Donor-site Morbidity"; Joshua Tam, PhD. et al.; DOI: 10.1097/GOX.0b013e3182a85a36; Jan. 18, 2013 (9 pages).

"The use of the Meek technique in conjunction with cultured epithelial autograft in the management of major paediatric burns"; Seema Menon et al.; JBUR-3864; No. of pp. 6; Sep. 6, 2012; (6 pages).

"Microskin grafting.I. Animal experiments"; Zhang Ming-liang et al.; 540 Burns (1986) 12, (8), Jul. 8, 1986; 540-543; (4 pages).

"Microskin grafting.II. Clinical report"; Zhang Ming-liang et al.; Burns (1986) 12, (8) Jul. 8, 1986; 544-548; (6 pages).

"Microscopic Split-Skin Grafts: A New Technique for 30-Fold Expansion"; Stephen D. Blair et al.; The Lancet, Aug. 29, 1987 (2 pages).

"Epidermal Regeneration by Micrograft Transplantation with Immediate 100-Fold Expansion"; Florian Hackl, M.D. et al.; vol. 129, No. 3; Sep. 7, 2011; (10 pages).

"Innovations in Caring for a Large Burn in the Iraq War Zone"; Roy R. Danks, Do, et al.; Journal of Burn Care & Research Jul./Aug. 2010; J Burn Care Res 2010; 31:665-669 (5 pages).

"Moist dressing coverage supports proliferation and migration of transplanted skin micrografts in full-thickness porcine wounds"; Florian Hackl et al.; Burns 40 (2014) 274-280; Jun. 3, 2013 (7 pages).

"Sandwich-type Fiber Scaffolds with Square Arrayed Microwells and Nanostructured Cues as Microskin Grafts for Skin Regeneration"; Bing Ma et al.; Biomaterials. Jan. 2014; (24 pages).

Xpansion Micro-Autografting Kit; Applied Tissue Technologies, LLC; 99 Derby Street, Suite 200, Hingham, MA; Item #00-321; Revised Oct. 2017 (1 page).

"Practice of split-thickness skin graft storage and histological assessment of tissue quality"; Alicia Knapik et al.; Journal of Plastic, Reconstructive & Aesthetic Surgery (2013) 827-834; Aug. 22, 2012; (8 pages).

Xpansion; ACELL; <URL:http://acell.com/xpansion/ retrieved Aug. 23, 2018>; Revised Nov. 17, 2017 (2 pages).

U.S. Appl. No. 62/564,745, filed Sep. 28, 2017, Bing Ma.

* cited by examiner

NEEDLE ARRAY GUIDE FOR SKIN GRAFT EXPANSION APPARATUS, SKIN GRAFT EXPANSION APPARATUS AND SKIN GRAFTING SYSTEM INCLUDING THE SAME, AND RELATED METHODS AND COMPONENTS

CROSS-REFERENCE TO RELATED APPLICATIONS

This application is based upon and claims priority benefit of U.S. Provisional Patent Application No. 62/564,745, filed Sep. 28, 2017, the entire contents of which are incorporated herein by reference.

BACKGROUND

1. Field

The present disclosure relates to skin grafting apparatuses and systems and, in particular, to skin grafting apparatuses and systems that spread minced donor skin to a larger coverage area, as well as methods of using such apparatuses and systems.

2. Related Art

Large, full-thickness skin defects resulting from burns, soft tissue trauma, chronic ulcers, scar surgery, congenital giant nevi, and diseases leading to skin necrosis represent a significant clinical problem that is far from being solved (see Bottcher-Haberzeth S, Biedermann T, Reichmann E. Tissue engineering of skin. *Burns*. 2010; 36(4): 450-60; Maruccia M, Onesti M G, Sorvillo V, et al. An alternative treatment strategy for complicated chronic wounds: negative pressure therapy over mesh skin graft. *Biomed Res Int* 2017; 2017: 8395219. Doi:10.1155/2017/8395219; Heidekrueger P I, Broer P N, Tanna N, et al. Postburn head and neck reconstruction: an algorithmic approach. *J Craniofac Surg*. 2016; 27(1): 150-5). Skin tissue engineering is believed to be a promising strategy to address this clinical problem. The ability to grow keratinocytes in vitro and generate cohesive sheets of stratified epithelium which maintains the characteristics of authentic epidermis was developed by Rheinwald and Green in 1975 and is the most commonly used technology for producing graftable epithelia (see Rheinwald J G, Green H. Serial cultivation of strains of human epidermal keratinocytes: the formation of keratinizing colonies from single cells. *Cell*. 1975; 6(3): 331-43). The first clinical application was reported by O'Connor et al. in 1981 (see Ronfard V, Rives J M, Neveux Y, et al. Long-term regeneration of human epidermis on third degree burns transplanted with autologous cultured epithelium grown on a fibrin matrix. *Transplantation*. 2000; 70(11): 1588-98). Cultured dermo-epidermal skin substitutes have also been developed in recent years (see Pham C, Greenwood J, Cleland H, et al. Bioengineered skin substitutes for the management of burns: a systematic review. *Burns*. 2007; 33: 946-57).

However, none of the skin substitutes can address the unique complex networks of dermal papillae in the dermal-epidermal junction, which are finger-like structures of the dermis projecting upwards into the epidermis (see Chan L S. Human skin basement membrane in health and in autoimmune disease. *Front Biosci*. 1997; 15(2): d343-52). As a result, when the cultured epidermal autografts (CEA) were transplanted on burn wounds, all of the patients experienced skin fragility in the autografts sites (see Woodley D T, Peterson H D, Herzog S R, et al. Burn wounds resurfaced by cultured epidermal autografts show abnormal reconstitution of anchoring fibrils. *JAMA*. 1988; 259(17): 2566-71). Besides, questions related to optimal cell type for culture, culture techniques, transplantation of confluent sheets or non-confluent cells, immediate and late final take, carrier and transfer modality, as well as final outcome, ability to generate an epithelium after transplantation, and scar quality are still not fully answered (see Atiyeh B S, Costagliola M. Cultured epithelial autograft (CEA) in burn treatment: three decades later. *Burns*. 2007; 33(4): 405-13). In fact, the dermal component of skin determines the mechanical (resistance to pressure and shear forces, graft shrinkage), functional (sensibility), and aesthetic properties of the graft (see Hierner R, Degreef H, Vranckx J J, et al. Skin grafting and wound healing—the "dermato-plastic team approach". *Clin Dermatol*. 2005; 23: 343-52).

Therefore, split-thickness skin autografts (STSG) are still the "gold standard" for burn wound closure and the mainstay of treatment for permanent wound coverage and healing (see Orgill D P. Excision and skin grafting of thermal burns. *N Engl J Med*. 2009; 360(9): 893-901). Importantly, STSG contains complex skin structures including whole or partial hair follicles, sweat glands, sebaceous glands, dermal and epithelial stem cells, epidermal pigmentation, and vessels. For these reasons, STSG keeps most of the function of skin in addition to physical barrier for human body.

Some of the main challenges for STSG encountered are the following. First, there is donor site shortage for STSG when the burn wound over 50-60% of the total body surface area (TBSA) (see Loss M, Wedler V, Kunzi W, et al. Artificial skin, split-thickness autograft and cultured autologous keratinocytes combined to treat a severe burn injury of 93% of TBSA. *Burns*. 2000; 26: 644-52). Second, donor site wounds are very painful and lead to scarring. Scar tissue is stiff, often painful, dysfunctional, and tends to contract over time, causing deformities (see Tam J, Wang Y, Farinelli W A, et al. Fractional skin harvesting: autologous skin grafting without donor-site morbidity. *Plast Reconstr Surg Glob Open*. 2013; 1(6): e47). Therefore, skin expansion techniques provide an alternative method to address these problems by decreasing the size of donor site to repair a large wound. Tanner and Vandeput introduced the mesh skin graft with a 1 to 3 ratio of donor area to recipient area in 1964 (see Tanner J C Jr., Vandeput J, Olley J F. The mesh skin graft. *Plast Reconstr Surg*. 1964; 34: 287-92).

The mesh skin graft technique is commonly used in hospitals around the world, but it cannot acquire an expansion ratio that is larger than 1:6 (an expansion ratio larger than 1:6 is an expansion ratio of 1:x where x is a number larger than 6). C. P. Meek in 1958 developed the MEEK technique which can reach expansion ratios of up to 1:9. Modified MEEK skin graft technique has won great success in treatment of severe burn injury in recent years (see Menon S, Li Z, Harvey J G, et al. The use of the MEEK technique in conjunction with cultured epithelial autograft in the management of major paediatric burns. *Burns*. 2013; 39(4): 674-9). However, the MEEK technique can only reach a maximum expansion ratio of 1:9. The limitation for the MEEK technique is that the minimum size of skin graft which MEEK autograft can achieve is 3×3 mm, because a special glue must be applied on the epidermal side of the autografts in order to adhere on gauze. Another limitation for the MEEK technique is the thickness of graft. The technique requires harvesting a very thin donor skin less than 0.15 mm thickness. Otherwise, the harvested donor skin will curve and become impossible to process. An inappropriate thickness may occur when the surgeon does not have sufficient experience in MEEK graft. Further, the thin STSG will be more contractive on a wound bed than a thick STSG.

A large skin expansion ratio has been achieved by cutting the skin grafts into a smaller size. Zhang M L, et al. succeeded in repairing burn wounds by mincing skin grafts into 1×1 mm and realized an expansion ratio of 1:15 in 1986 (see Zhang M L, Chang Z D, Han X, et al. Microskin grafting. I. Animal experiments. *Burns Incl Therm Inj.* 1986; 12(8): 540-3; and Zhang M L, Wang C Y, Chang Z D, et al. Microskin grafting. II. Clinical report. *Burns Incl Therm Inj.* 1986; 12(8): 544-8). Stephen D B, et al. developed a method to mince skin into 200×200 for 30-fold expansion and successfully treated five patients with venous ulcers in 1987 (see Stephen D B, Jagdeep N, Christopher M B, et al. Microscopic split-skin grafts: a new technique for 30-fold expansion. *The Lancet;* 1987; 2(8557): 483-4). E Eriksson reported a novel method which minced skin graft into 0.8×0.8 mm parts and transplanted the minced parts to the wound in a 100-fold expansion (see Florian H, Juri B, Scott R G, et al. Epidermal regeneration by micrograft transplantation immediate 100-fold expansion. *Plast Reconstr Surg.* 2012; 129(3): 443e-52e). Dr. Eriksson also disclosed a special tool to prepare the microskin grafts. This product is commercialized as XPANSION Micro-autografting kit by SteadMed Medical, TX, USA. The instrument was used to successfully rescue the life of a severe burn injured patient during the Iraq war by Dr. Roy R D (see Roy R D, Kimberly L. Innovations in caring for a large burn in the Iraq war zone. *J Burn Care Res.* 2010; 31: 665-9). However, Dr. Roy found that placement of the graft was extremely time intensive. It required much more time to cover the wound than was necessary to cover with standard skin grafting. Importantly, the XPANSION Kit results in clumps or aggregates of skin particles without even distribution between grafts on wound bed. For this reason, the desired large expansion ratios by using microskin grafts less than 1×1 mm are not successful in clinical application (see http://www.steadmed.com/xpansion/).

SUMMARY

Currently, there are at least two problems which hinder the clinical application of microskin grafting techniques. First, the tiny pieces of microskin grafts cannot be placed on the wound bed with an even distribution between skin graft islands. Second, placement of microskin grafts on the wound bed is extremely time- and labor-intensive. A sandwich-type nanofiber scaffold to carry and fix the skin particles on wound bed has been proposed. As a result, the desired inter-particle distance for a given large expansion ratio can be realized (see Ma B, Xie J, Jiang J, et al. Sandwich-type fiber scaffolds with square arrayed microwells and nanostructured cues as microskin grafts for skin regeneration. *Biomaterials.* 2013; 35(2): 630-41; and Xie J, Ma B. Nanofiber scaffolds and methods for repairing skin damage. U.S. Patent Application Publication 2014/0004159 A1). The above demonstrates the concept that a scaffold (i.e., nanofiber, gauze, etc.) can be used as a carrier to hold, transfer and keep the evenly distributed skin grafts on the wound bed.

There is a need for a method that can quickly load a large number of tiny skin particles at a large expansion ratio on a scaffold or other carriers to address the issue of the time and labor involved. Loss of viable cells in the graft will cause skin grafting failure. The most important reasons that cells in microskin graft have limited viability include: (1) the lack of blood supply for harvested graft, and (2) the drying of tissue in air exacerbated due to the small tissue volume of the minced skin particles (see Hackl F, Kiwanuka E, Philip J, et al. Moist dressing coverage supports proliferation and migration of transplanted skin micrografts in full-thickness porcine wounds. *Burns.* 2014; 40(2): 274-80; Knapik A, Kornmann K, Kerl K, et al. Practice of split-thickness skin graft storage and histological assessment of tissue quality. *J Plast Reconstr Aesthet Surg.* 2013; 66(6): 827-34). 70% of skin tissue volume is water. For reason of a large surface area, water is easy evaporated from the tiny microskin graft. Therefore, microskin grafting is very time-sensitive. High-speed skin transfer is a key issue to ensure a high viability of cells that are transplanted on wound. Therefore, a new technique to increase the time efficiency of the microskin grafting process is highly desirable.

One aspect of the disclosure is a needle array guide for a skin graft expansion apparatus. The needle array guide includes: a lower side having openings; and guide channels respectively leading to the openings and converging closer toward one another as the guide channels approach the openings, the guide channels configured to receive a plurality of hollow needles, arranged in a needle array and having respective tips to be attachable to minced skin particles obtained from a skin graft, to thereby guide movement of the plurality of hollow needles when the plurality of hollow needles are being protruded from the openings toward the minced skin particles and when the plurality of hollow needles are being retracted toward the openings.

Another aspect of the disclosure is a needle array apparatus for a skin graft expansion apparatus. The needle array apparatus includes a platform and a needle array including a plurality of hollow needles attached to the platform. The plurality of hollow needles have respective tips to be attachable to minced skin particles obtained from a skin graft, and are configured to be guided so as to converge closer to one another at a tip end of the needle array.

Another aspect of the disclosure is a skin graft expansion apparatus that includes the needle array guide and the needle array apparatus. The plurality of hollow needles of the needle array apparatus are received in the guide channels of the needle array guide so as to be guided by the guide channels when moving relative to the needle array guide. The tips of the plurality of hollow needles are protrudable out of the openings toward the minced skin particles and retractable into the openings.

According to other aspects of the disclosure, the skin graft expansion apparatus may be included as part of a skin grafting system and may be used in a method of transporting tissue from a donor skin graft to a carrier. Another aspect of the disclosure is a cutting board for this and other skin grafting systems.

Others aspects and advantages will become apparent and more readily appreciated from the following description of the embodiments, taken in conjunction with the accompanying drawings.

DESCRIPTION OF EMBODIMENTS

Figure 1:
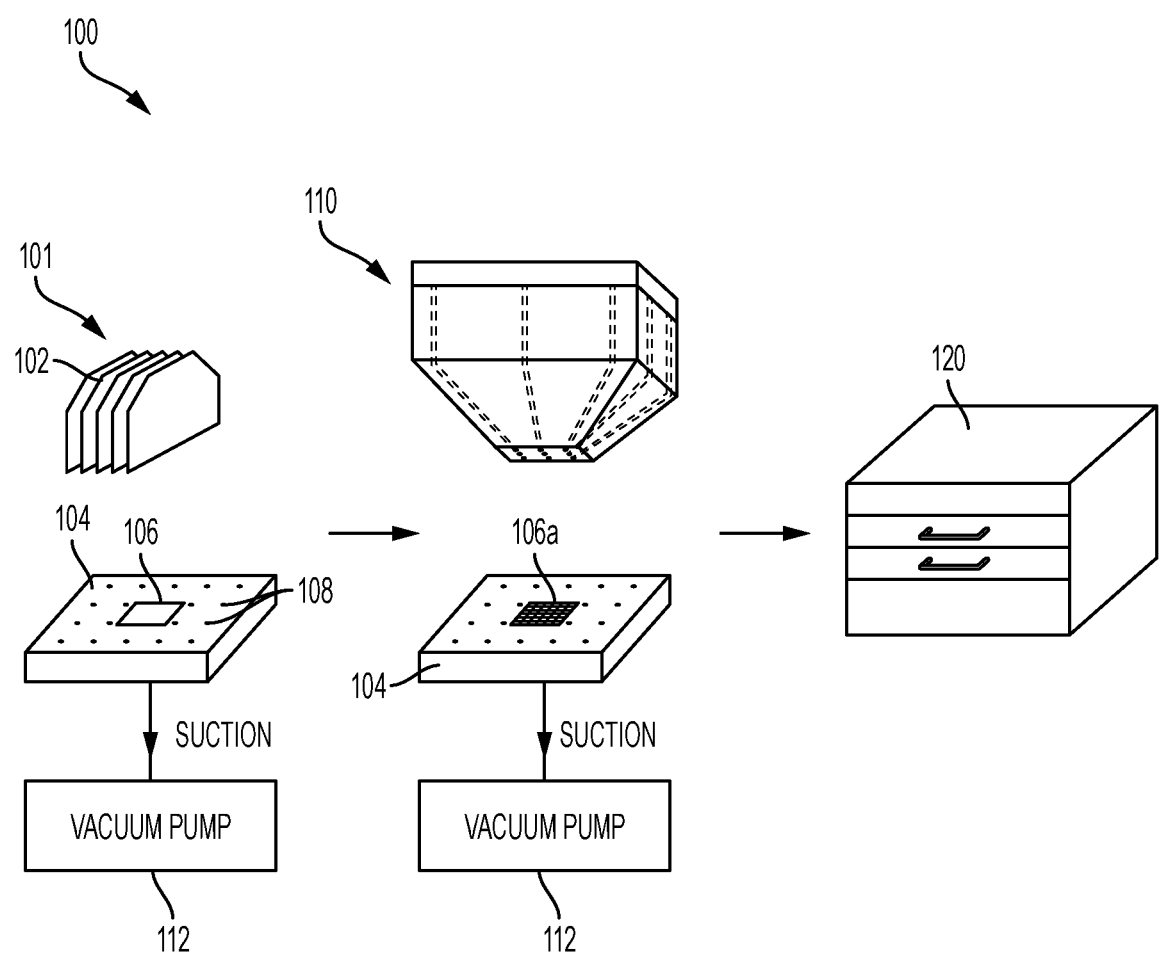
FIG. 1 illustrates a skin grafting system according to one or more embodiments of the present disclosure.

Hereinafter, embodiments will be described. The description and illustrations are illustrative in nature and are not intended to limit the scope of the claims. Furthermore, it should be understood that details may be omitted when not necessary for an understanding of the embodiments. In the drawings, like numerals represent like components. As used in this disclosure, the singular forms of terms (including terms preceded by "a" or "an") have a scope of one or more of the referents, unless the context clearly indicates otherwise. The term "or" generally has the meaning of an inclusive "or," as opposed to a mutually-exclusive "or," unless the context clearly indicates otherwise. When any component is referred to as being "connected to" another component, it should be understood that the components may be connected directly to each other or be connected to each other through one or more other components. Whenever a numerical range is given, the description of the range should be considered to have specifically disclosed all possible individual numerical values and sub-ranges within that range.

FIG. 1 illustrates a skin grafting system 100 including a skin graft expansion apparatus 110. The system 100 may also include a skin graft cutter 101, a cutting board 104, and a moisture chamber 120. For simplicity of illustration, other possible components of the system 100 (which are illustrated in other figures) have been omitted from FIG. 1.

The skin graft expansion apparatus 110 is used to expand a donor skin graft 106 after the donor skin graft 106 has been minced into a plurality of minced skin particles.

The minced skin particles to be expanded by skin graft expansion apparatus 110 may be prepared by any suitable method appreciated by those skill in the art. For example, the minced skin particles expanded by skin graft expansion apparatus 110 may be prepared by using the cutting board 104 and the skin graft cutter 101 of the skin grafting system 100 in the following manner. A donor skin graft 106 is placed on the cutting board 104. Then, the skin graft cutter 101 cuts the donor skin graft 106 to obtain a minced skin graft 106a, which comprises a plurality of minced skin particles (also referred to as "microskin graft").

The skin graft cutter 101 may be any device that is capable of cutting donor skin graft 106 into a minced skin graft 106a. For example, the skin graft cutter 101 may include a plurality of parallel blades 102. The parallel blades 102 may be distanced apart from each other at a distance that is the same or substantially the same as the desired size of the minced skin graft 106a. When the skin graft cutter 101 cuts of the donor skin graft 106, the cutting should be performed so as to disturb the donor tissue of the donor skin graft 106 as little as possible. The parallel blades 102 have a sharpness suitable for its function of cutting skin graft, and may therefore have extremely high sharpness.

The cutting board 104 may have holes 108 formed into its surface. The holes 108 may be connected to a vacuum pump 112 configured to apply a constant level of vacuum pressure (suction) such that air on the surface of the cutting board 104 would be suctioned into the holes 108 by vacuum suction. The vacuum suction, which tends to bring air inward into the holes 108 caused by the vacuum, holds the donor skin graft 106 in place and prevents it from curling while the skin graft 106 is being cut by the skin graft cutter 101. The holes 108 may be of any spacing, size, or configuration suitable for holding the donor skin graft 106 in place. The holes 108 may be connected to the vacuum pump 112 through interior air channels located within the body of the cutting board 104.

The cutting board 104 may be a Teflon block or cork, or other suitable materials. Alternatively or additionally, a metal chamber (not shown) with striped windows may be used to keep the donor skin graft 106 in place.

Figure 2A:
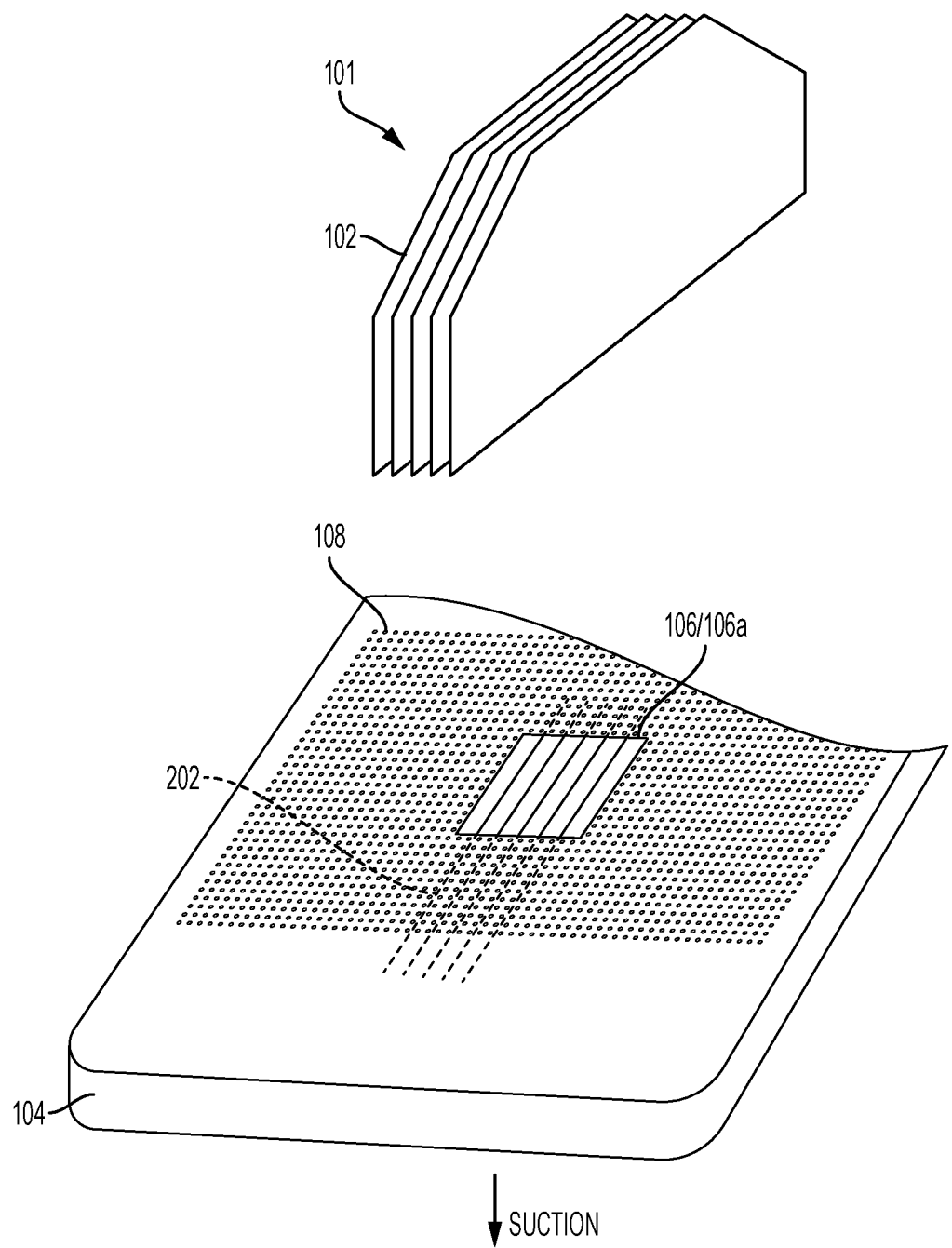
FIGS. 2A-2C illustrate a skin graft cutter and a cutting board, and a process using the skin graft cutter and the cutting board according to one or more embodiments of the present disclosure.
Figure 2B:
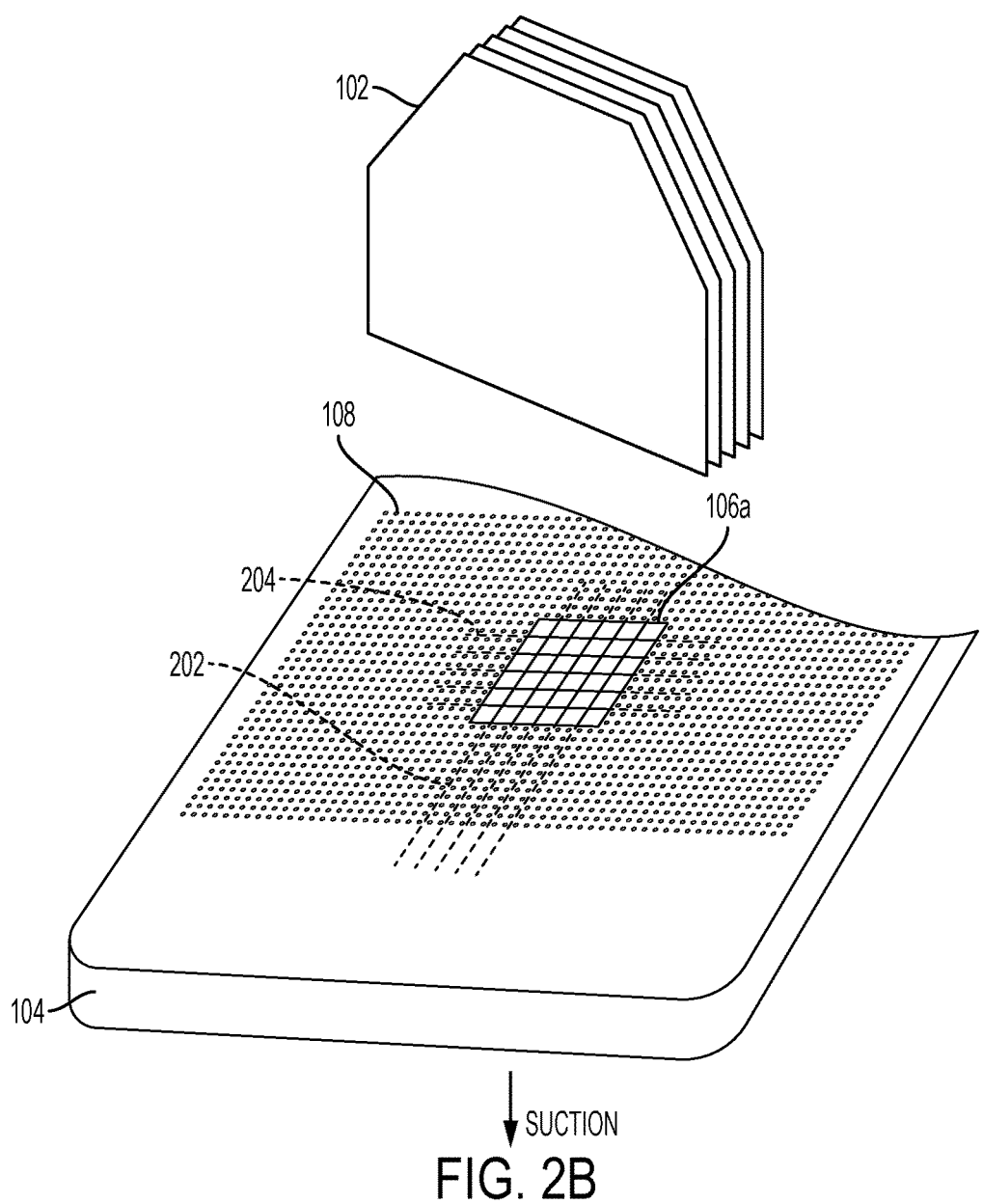
Figure 2C:
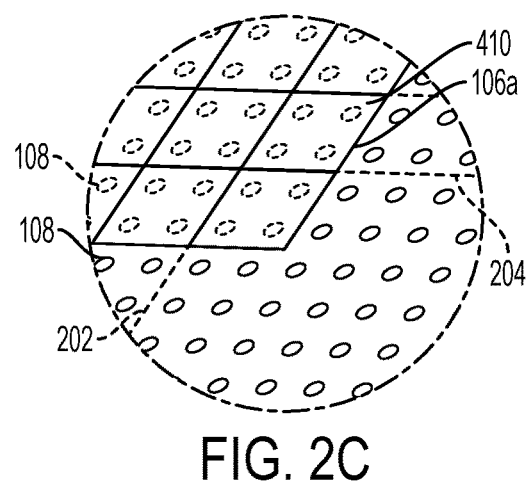

FIGS. 2A-2C show an example operation of the skin graft cutter 101 on the cutting board 104, in the case in which the skin graft cutter 101 is formed by a plurality of parallel blades. In order to mince the donor skin graft 106, the skin graft cutter 101 may first perform cuts oriented along a first direction as indicated by lines 202 shown in FIG. 2A, and then perform cuts oriented along a second direction as indicated by lines 204 shown in FIG. 2B. Accordingly, the minced skin graft 106a is formed as an array of minced skin particles 410 having been cut from each other by the skin graft cutter 101. In FIGS. 2A-2B, lines 202 and 204 show the positions at which the parallel blades 102 of the skin graft cutter 101 are applied to the donor skin graft 106 and the cutting board 104. The first and second directions may be substantially perpendicular to each other, as shown, but may also be oriented in other manners.

As illustrated in FIGS. 2A-2C, the cutting board 104 may have holes 108, which are connected to vacuum pump 112 configured to apply the aforementioned vacuum suction to hold the donor skin graft 106 in place during and after the cutting process. FIG. 2C is a close-up view of the lower-right corner of the donor skin graft 106 shown in FIG. 2B. FIG. 2C shows the holes 108 on the surface of the cutting board 104, a portion of the holes 108 being underneath donor skin graft 106. The holes 108 may have a diameter in a range of from about 0.1 mm to about 0.2 mm.

The center-to-center distance (pitch) of the holes 108 may be smaller than the size of the minced skin particles 410 (e.g., smaller than about 1 mm) to provide an adequate coverage density. More particularly, the pitch may be approximately half the size of the minced skin particles 410 or smaller. For example, the pitch may be about 0.5 mm or less than 0.5 mm, which would be suitable when the size of the minced skin particles 410 to be obtained in the cutting process is 1×1 mm. The holes 108 may be arranged in a square-grid arrangement (as shown) with the aforementioned pitch. However, the disclosure is not limited thereto, and other arrangements of the holes 108 are also possible, such as a hexagonal arrangement with the aforementioned pitch.

Figure 3A:
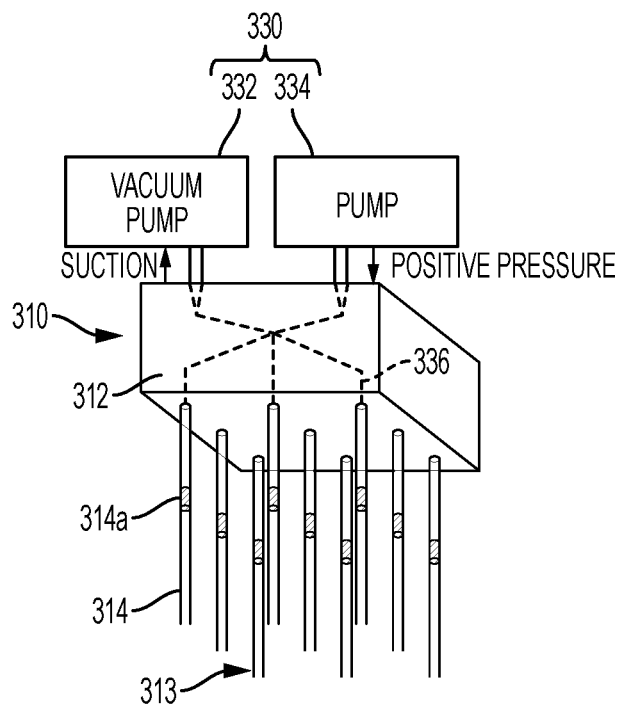
FIGS. 3A-3C illustrate a skin graft expansion apparatus including a needle array guide, along with other components of the skin grafting system, according to one or more embodiments of the present disclosure.
Figure 3B:
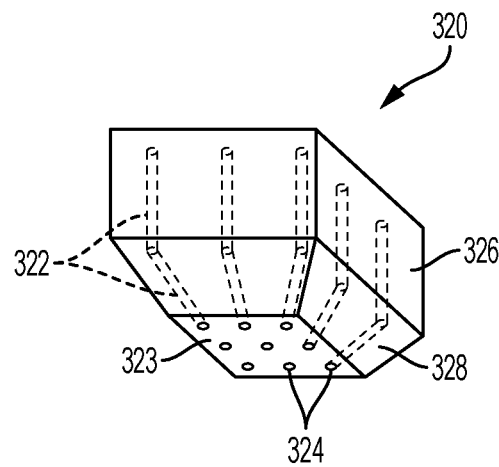
Figure 3C:
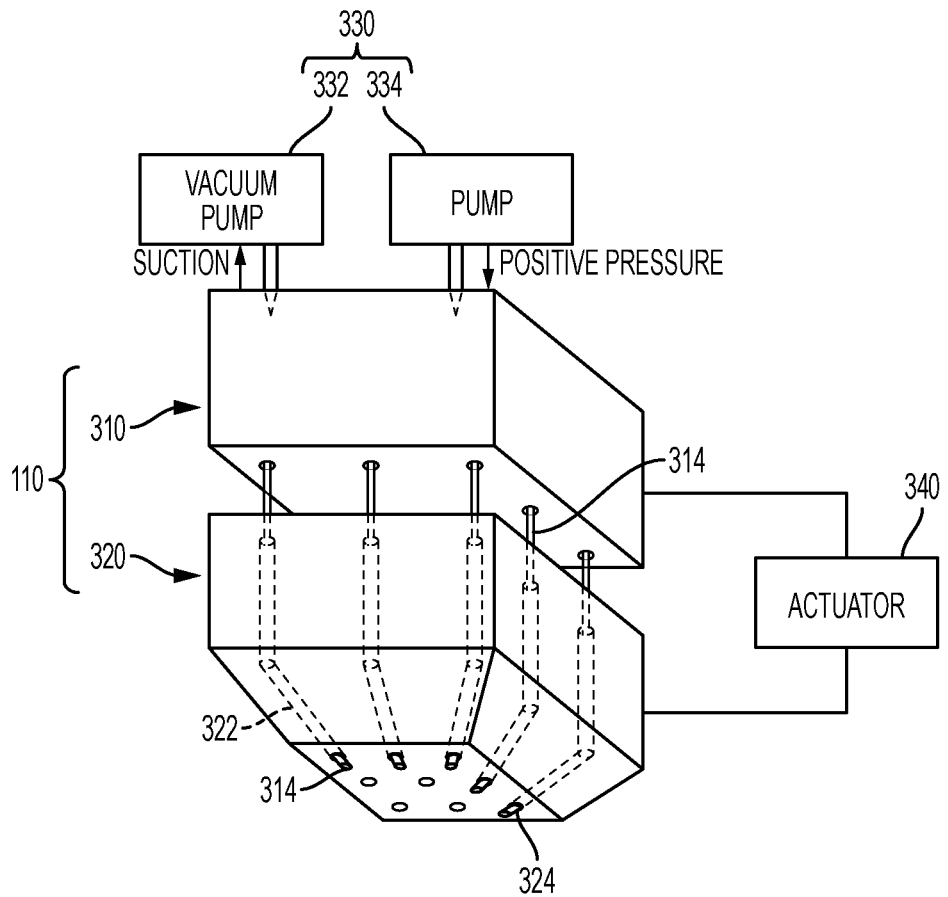

FIGS. 3A-3C illustrate a configuration of the skin graft expansion apparatus 110. A component of the skin graft expansion apparatus 110 is a needle array guide 320 having openings 324 on a lower side of the needle array guide 320 and guide channels 322 leading to respective openings 324, the guide channels 322 converging closer toward one another as the guide channels 322 approach the openings 324. The guide channels 322 are configured to receive a plurality of needles (e.g., needles 314 discussed below), such needles being arranged in a needle array (e.g., needle array 313 discussed below) and having respective tips to be attachable to minced skin particles 410 obtained from skin graft 106, to thereby guide movement of the plurality of needles when the plurality of needles are being protruded from the openings 324 toward the minced skin particles and when the plurality of needles are being retracted toward the openings 324.

The skin graft expansion apparatus 110 further includes a needle array apparatus 310 including a platform 312 and a needle array 313 including a plurality of needles 314 attached to the platform 312. The plurality of needles 314 have respective tips to be attachable to minced skin particles 410 obtained from the skin graft 106. The plurality of needles 314 are received in the guide channels 322 such that the plurality of needles 314 are guided by the guide channels 322, and the tips of the plurality of needles 314 are protrudable from the openings 324 toward the minced skin particles 410 and are then retractable back toward the openings 324. The skin graft expansion apparatus 110 may be configured such that the tips of the plurality of needles 314 have a retracted position within the needle array guide 320, and the tips are protrudable out of the openings 324 (from the retracted position within the needle array guide 320) and then retractable back into the openings 324.

As shown in FIG. 3A, the needle array apparatus 310 includes a platform 312 serving as a base on which the needle array 313 is fixed. The needles 314 may be hollow to permit passage of air through the needles 314. FIG. 3A shows a 3×3 example of the needle array 313 for purposes of illustration. In actual implementation, the needle array may also be of 5×5, 10×10, 20×20, or larger sizes. In these examples, total number of needles may therefore be 9, 25, 100, and 400, respectively. Additionally, the needle array 313 is not limited to two-dimensional arrangements, but may also be in a one-dimensional linear arrangement. When the needle array 313 has a two-dimensional arrangement, the overall form of the needle array 313 is not limited to a rectangular form, but may have an overall round, oval, or irregularly-shaped form. The needles 314 on the needle array 313 may be evenly distributed, but are not limited to such configuration.

FIG. 3B illustrates the needle array guide 320. The needle array guide 320 is configured to guide the needles 314 of the needle array 313 when the needles 314 are received into and guided through the needle array guide 320. The needle array guide 320 includes an array of a plurality of hollow guide channels 322 designed to guide the needles 314 such that the needles, after passing through the needle array guide 320, exit in a formation in which the tips of the needles 314 are converged to be closer to one another as compared to the state prior to exiting the guide channels 322. In other words, as the tips of the needles 314 move outward from the openings 324, the needle array guide 320 converges the needles 314 toward one another so as to decrease the pitch of the needle tips. In guiding the needles 314 in this manner, the needle array guide 320 may be considered as a converging guide for needles.

In order to guide the needles 314 in the above manner, the guide channels 322 converge closer toward one another as the guide channels 322 approach the openings. For example, all or a subset of the guide channels 322 may be angled in a converging manner in approaching the openings 324, such that the tips of the plurality of needles 314 converge closer toward one another when the plurality of needles are guided out of the openings 324 and separate apart from each other when the plurality of needles 314 are retracted into the openings 322. As such, the guide channels converge the needles 313 onto a plane or surface that is smaller than the size of the array of openings 324. Such plane or surface may be a plane or surface on which the minced skin particles 410 are disposed. As noted above, it is possible that only a subset of the guide channels 322 are angled. For example, in a 3×3 configuration, only the eight outer channels need to be angled, and the central channel may be straight. In a 5×5 configuration, the central channel may be straight, while the other channels are angled progressively more steeply toward the outer periphery.

The needle array guide 320 may have: an upper body portion 326, serving as a base portion, in which the guide channels 322 may be substantially parallel with each other; and a lower body portion 328, in which the guide channels 322 are converging closer toward one another as they approach the opening. The upper body portion 326 and the lower body portion 328 may serve the purpose of holding the guide channels 322 in place. Thus, they may be of any shape or design that serves this purpose, and may have a shape that corresponds to the general shape of the array of guide channels 322. The upper body portion 326 may be a rectangular prism, which is suitable for the substantially parallel arrangement of the guide channels 322 in the upper body portion 326. The lower body portion 328 may be of a tapered shape whose width decreases from top to bottom, to match the angling of the guide channels 322 in the lower body portion 328. For example, the lower body portion 328 may be of a frusto-pyramidal shape as illustrated in FIGS. 3B-3C, but one skilled in the art would appreciate that other shapes are possible.

The openings 324 to which the guide channels 322 lead may be disposed in an array along the bottom or bottom surface 328 of the needle array guide 320. The openings 324 may be disposed in a two-dimensional array at a substantially regular distance along a first direction and at a substantially regular distance along a second direction substantially perpendicular to the first direction as illustrated in FIGS. 3B-3C, such that the expanded minced skin particles 410 can be distributed evenly.

The guide channels 322 may be constructed in any suitable manner. For example, the guide channels 322 may be implemented as a plurality of tubes, in which case the tubes may be held together by the upper body portion 326 and the lower body portion 328. The guide channels 322 may also be implemented as internal tunnels formed inside a continuous piece of material constituting the needle array guide 320 or any part thereof (including the aforementioned portions 326 and 328). The outer guide channels 322 may be disposed inside the outer periphery of the lower body portion 328, especially when the lower body portion 328 has a shape whose width decreases from top to bottom, and may also be disposed inside the outer periphery of the upper body portion 326, as shown in FIG. 3B and other figures. Thus, all guide channels 322 may be disposed within the upper body portion 326 and/or the lower body portion 328. The upper body portion 326, the lower body portion 328, and the needle array guide 320 in general may be made, in whole or in part, of any suitable material, including metals, plastics, ceramics, and composite materials.

The openings of the needles 314 and the openings 324 of the guide channels 322 both have diameters that are smaller than the minced skin particles, in order to prevent the minced skin particles from being sucked into the needles 314 or the guide channels 322. The interior of the guide channels 322 may have a size (inner diameter) that fits the needles 314 tightly inside the guide channels 322 (to prevent pressure loss when used with the pump system described below) and is smaller than the minced skin graft.

The number of needles 314, the number of guide channels 322, and the number of openings 324 included in the skin graft expansion apparatus 110 may each be a respective quantity that is, for example, at least 3 and up to 10,000. It is noted that any quantity or sub-range within the range of 3 to 10,000 should be considered as having been specifically disclosed by this disclosure. Example quantities include 3, 4, 9, 16, 25, 100, 400, 1000, 5000, and 10,000. Any range of quantities between any two of the foregoing quantities, inclusive of endpoints, should be considered as having been specifically disclosed (e.g., ranges of 9 to 16, 9 to 25, 9 to 100, 9 to 400, 9 to 1000, 25 to 400, and 4 to 5000). One skilled in the art would appreciate that the quantity of these elements depends on the number of minced skin particles 410 to be concurrently picked up, and thus may be of any suitable amount. A quantity of 2 or a quantity greater than 10,000 of these elements may also be used. Since each needle 314 may be guided by a respective guide channel 324, the number of guide channels 322 and the number of openings 324 may be the same as the number of needles 314 in the needle array 313, but the disclosure is not limited thereto; for example, the number of guide channels 322 and the number of openings 324 may be greater than the number of needles 314.

The skin grafting system 100 may include a pump system 330 connected to the needles 314, configured to vacuum the hollow interior of the needles 314 to allow the needles to convey a vacuum suction effect, and also to apply positive pressure to the hollow interior of the needles 314. To realize these functionalities, the pump system 300 may include a vacuum pump 332 configured to create vacuum pressure in the needles 314 by way of suction, and a pump 334 configured to supply (positive) air pressure to the needles 314. As illustrated in FIG. 3A, the pumps may be connected to an exterior side (e.g., the top) of the needle array apparatus 310. For example, the interiors of the needles 314 may be connected to the outlets/inlets of the pump 332 and vacuum pump 334 through channels 336, which may be formed in the interior of the platform 312 of the needle array apparatus 310 (as shown in FIG. 3A) or provided as tubing. The channels 336 may connect to the interiors of each of the needles 314; however, for simplicity, channels 336 are shown only for a few of the needles 314 in FIG. 3A.

FIG. 3C shows the graft expansion apparatus 110 when the needle array 313 has been inserted into the needle array guide 320. Because the guide channels 322 are angled in the aforementioned converging manner, the guide channels 322 come closer toward one another along the downward direction. Thus, the pitch or spacing between the tips of the needles 314 can be changed when they are moving with the guidance of the guide channels 322. As the needles 314 move further downward, their tips come closer toward one another (so as to decrease the pitch or spacing between the tips). By moving the needles 314 downward, the pitch or spacing between the needles 314 can thus be adjusted to match the positions of the processed skin grafts.

Figure 4A:
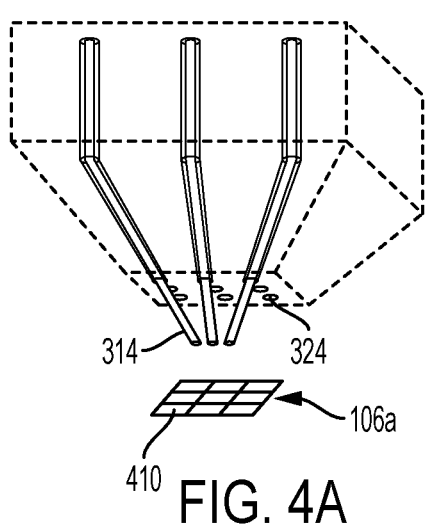
FIGS. 4A-4C illustrate a process of using the skin graft expansion apparatus according to one or more embodiments of the present disclosure.
Figure 4B:
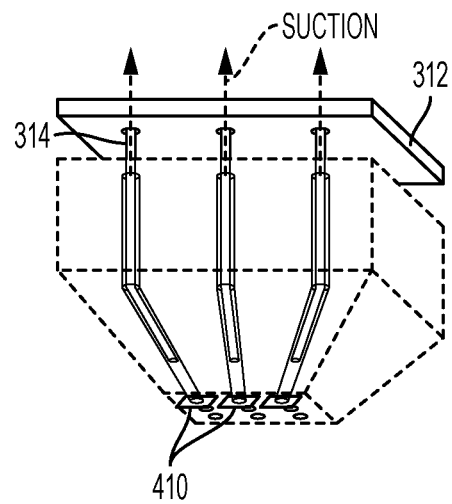
Figure 4C:
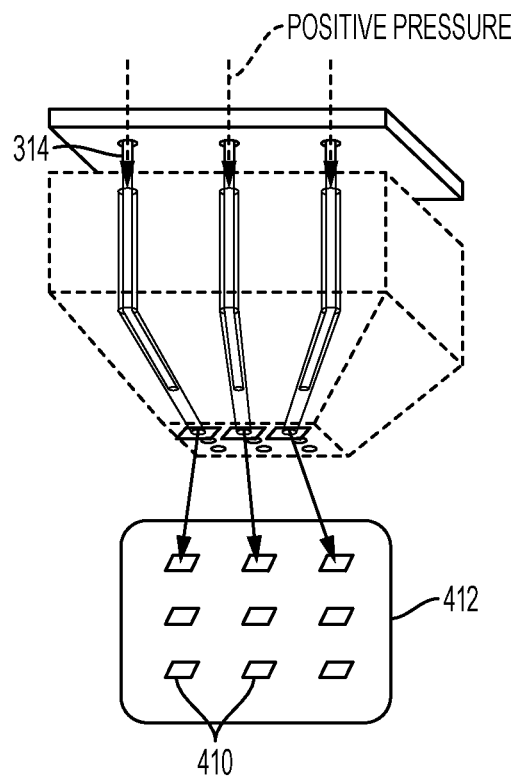

FIGS. 4A-4C illustrate an operation of the graft expansion apparatus 110. For purposes of illustration only, the size of the minced skin particles 410 of the minced skin graft 106a relative to the size of the array of the openings 324 on the bottom of the skin graft expansion apparatus 110 has been exaggerated. Additionally, only the front row of guide channels 322 and needles 314 are illustrated.

FIG. 4A shows the needles 314 being extended to make contact with the minced skin graft 106a. When the needles 314 have made contact with the minced skin graft 106a, a vacuum pressure provided by vacuum pump 332 helps to hold minced skin particles (microskin graft) 410 on the needles 314. The skin graft expansion apparatus 110 may typically be constructed such that all or substantially all needles 314 of the needle array 313 substantially simultaneously make contact with the minced skin graft 106a as a result of the operation of the skin graft expansion apparatus 110.

The needles 314 are then drawn back slowly to move inside the guide channels 322. The minced skin particles 410 are transferred to the openings 324 of the guide channels 322 when the needles 314 are moved inside the guide channels 322. The vacuum power of vacuum pump 322 will hold the minced skin particles 410 on openings 324 on the bottom of the needle array guide 320, as shown in FIG. 4B. To facilitate this, the needles 314 may be fit inside the channels 322 to a tightness that sufficiently avoids pressure loss.

Thus, by using the graft expansion apparatus 110, the minced skin particles 410 are distributed at a desired expansion ratio. Then, the minced skin particles 410 can be transferred to a carrier 412 (for example: a gauze, nanofiber scaffold, etc.) by the following operation. When the needle array guide 320 is moved on the top of carrier 412, the vacuum pressure is released and a positive air flow from the pump system 330 helps drop the minced skin particles 410 to the right place on the carrier 412, as shown in FIG. 4C. The needle array guide 320 can be designed such that the distribution of the openings 324 on the bottom surface of the needle array guide 320 matches the desired distribution of minced skin particles.

The expansion ratio can be computed as the ratio of the overall coverage area of the minced skin particles 410 prior to the application of the graft expansion apparatus 110 to the overall coverage area of the array of minced skin particles 410 after expansion by the graft expansion apparatus 110. Moreover, the overall coverage area of the array of minced skin particles 410 after expansion is based on the coverage area of the array of the openings 324.

Figure 5A:
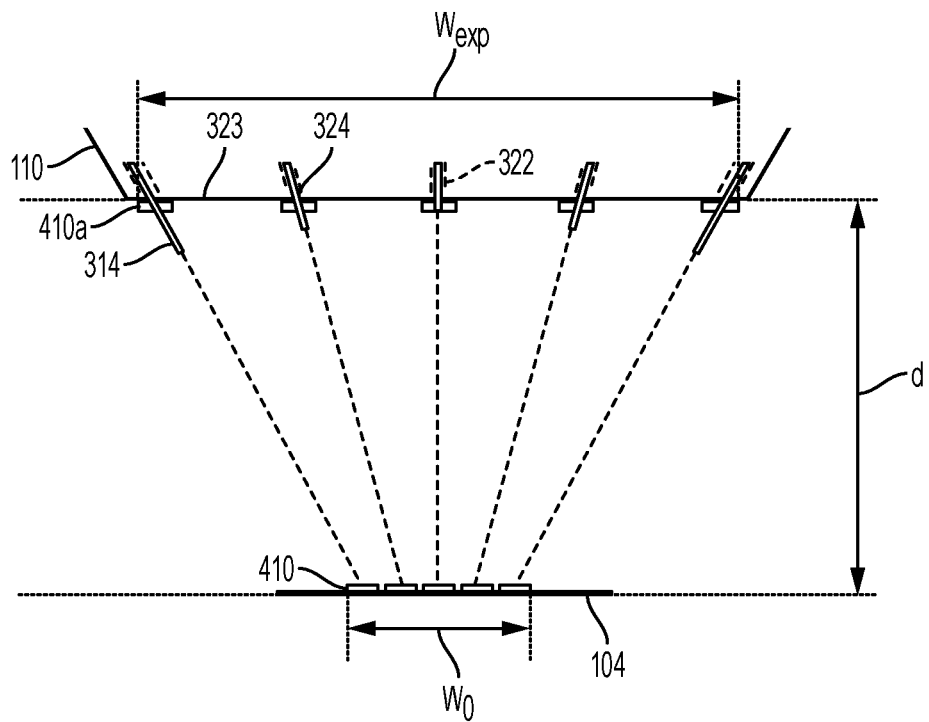
FIGS. 5A-5B illustrate variables affecting the expansion ratio when performing a process of using the skin graft expansion apparatus.
Figure 5B:
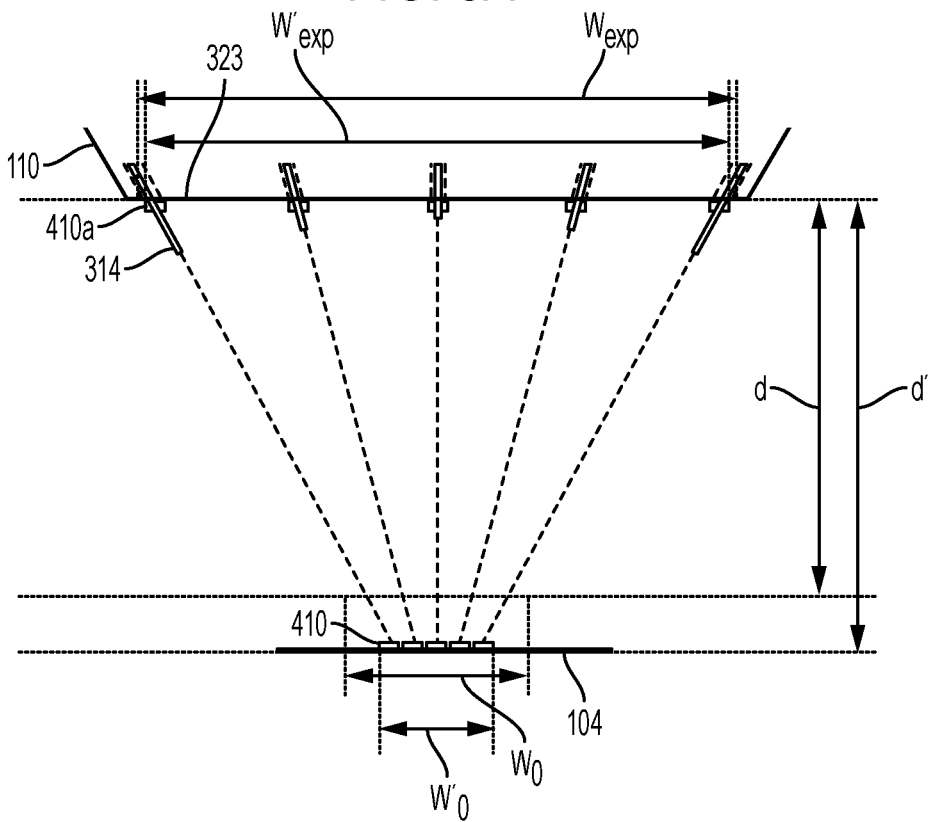

FIGS. 5A-5B illustrate the operation of the graft expansion apparatus 110 in expanding minced skin particles 410 to a certain expansion ratio. FIG. 5A shows a side or cross-sectional view of a needle array 313 with 5 needles along one dimension, such as a 5×5 array of needles. In this figure, $w_0$ is the width of coverage area of the minced skin particles 410 on cutting board 104, and d is the distance between the bottom 323 of the needle array guide 320 and the minced skin particles 410. The dashed lines extending from needles 314 show the paths of the needles 314 in converging onto the minced skin particles 410. By the operation of the needles 314 discussed in this disclosure, the minced skin particles 410 are expanded to a coverage area having an expanded width of $w_{exp}$. The minced skin particles 410, after being expanded to this width, are represented in this figure as expanded minced skin particles 410a. Assuming that these coverage areas are square (i.e., the length equals the width), the sizes of the coverage areas before and after expansion can be denoted by $w_0 \times w_0$ and $w_{exp} \times w_{exp}$, respectively. Thus, the expansion ratio is $1:((w_{exp} \times w_{exp})/(w_0 \times w_0))$.

FIG. 5B illustrates how the expansion ratio can be affected by the distance between the bottom 323 of the needle array guide 320 and the minced skin particles 410. For purposes of comparison, the measurements in FIG. 5A are also shown in FIG. 5B. In FIG. 5B, the minced skin particles 410 are now disposed at a distance d' (instead of d), and now have a coverage area width of $w_0'$ (instead of $w_0$) on the cutting board 401. In this case, the expansion ratio would be $1:((w'_{exp} \times w'_{exp})/(w'_0 \times w'_0))$, which is greater than the expansion ratio in the arrangement of FIG. 5A, since ($w'_0 \times w'_0$) is considerably smaller than ($w_0 \times w_0$), while ($w'_{exp} \times w'_{exp}$) is approximately the same as ($w_{exp} \times w_{exp}$) (slightly smaller than the latter due to the smaller skin particle size). Thus, by increasing the distance from d to d', the expansion ratio is increased, since the tips of the needles 314 converge progressively closer toward one another as this distance increases.

The skin graft expansion apparatus 110 according to this disclosure permits expansion ratios reaching 1:100 or higher (when the expansion ratio is expressed in the form "1:x", a larger "x" corresponds to a higher or larger ratio). For example, skin graft expansion apparatus 110 may be configured to expand the minced skin particles 410 at any expansion ratio within a range of 1:10 to 1:100 (such as 1:10, 1:12.5, 1:15, 1:17.5, 1:20, 1:25, 1:40, and 1:100). Such expansion ratios may be realized by a suitable combination of the geometric parameters of the needle array guide 322 (including the angles of the guide channels 322 and the spacing between the openings 324) and the distance d between the bottom 323 of the needle array guide 320 and the minced skin particles 104.

The diameters of the needles 314 may be about half the size of minced skin particles 410. For example, a minced skin particle 314 may have a size of about 1 mm or smaller, and a weight of about 0.001 g (close to the weight of water). With a diameter of about half the size of minced skin particles 410, the needles 314 can readily insert into the skin particle to allow easy pick-up of the skin particle, especially when vacuum pressure from the pump system 330 is applied.

Figure 6A:
FIGS. 6A-6C illustrate a needle of a needle array according to one or more embodiments of the present disclosure.
Figure 6B:
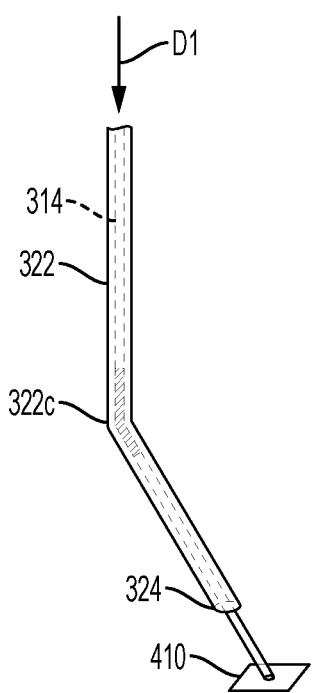

FIG. 6B illustrates an operation of passing needle 314 through guide channel 322 and out of opening 324 to contact with and hold minced skin particle 410 using vacuum pressure from vacuum pump 332. As shown, the needle is passed through the guide channel 322 in the direction D1. The bend of the tunnel at transition between the base 326 and the lower body portion 328 causes the needle 314 to bend at an intermediate section 314a. As the needle 314 contacts the minced skin particle, the vacuum pressure from the vacuum pump causes the minced skin particle 410 to be held onto the tip of the needle.

Figure 6C:
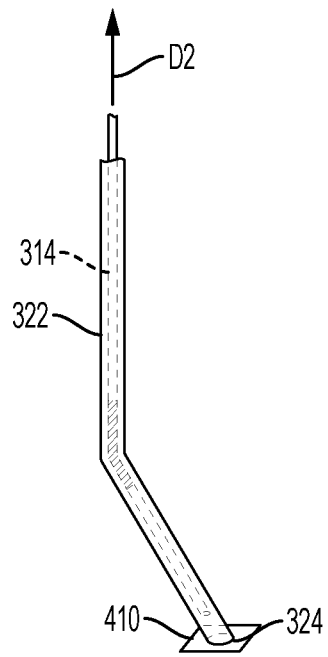

FIG. 6C illustrates an operation of retracting the needle in direction D2, such that the tip of needle 314 is retracted into the opening 324. In this stage, the minced skin particle 410 remains held to the surface by vacuum pressure applied to the needle 314.

The needles 314 may have any flexibility suitable for traversing through the guide channels 322 through at least a distance necessary to carry out the operations of protruding out of and retracting back into the openings 324. For example, referring to FIG. 3A and FIG. 6A, the needles 314 may be flexible in at least an intermediate section 314a that provides a sufficient range of movement for the needle's traversal around the bend 322c of the guide channels 322.

Flexible sections of the needle, such as the intermediate section 314a, may be constructed in a manner similar to needles flexible enough to flex inside a blood vessel. For example, the flexible sections of the needles 314 may have the design and construct of (or similar to) needles/catheters used in percutanous transluminal coronary angioplasty, which flexibly fit inside blood vessels. The remaining sections of the needle 314 above section 314a are not required to be flexible. For example, lower section 314b below section 314a may have a stiffness characteristic of surgical grade needles of similar size.

Figure 7A:
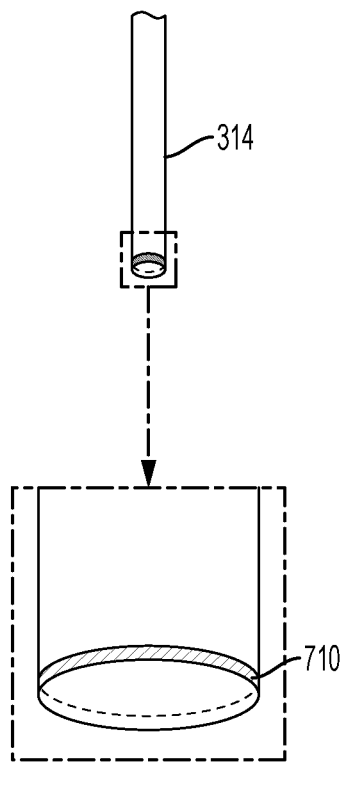
FIGS. 7A-7C illustrate possible structures for the tips of the needles of the needle array.
Figure 7B:
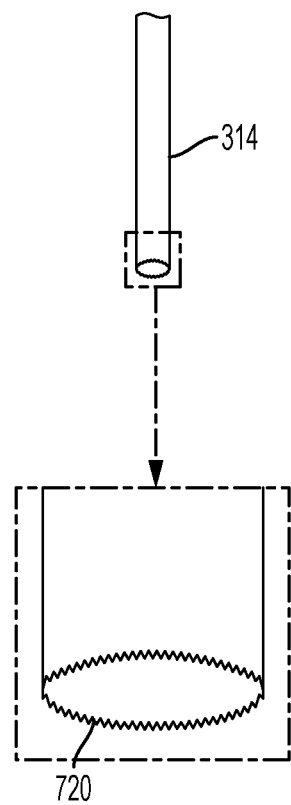
Figure 7C:
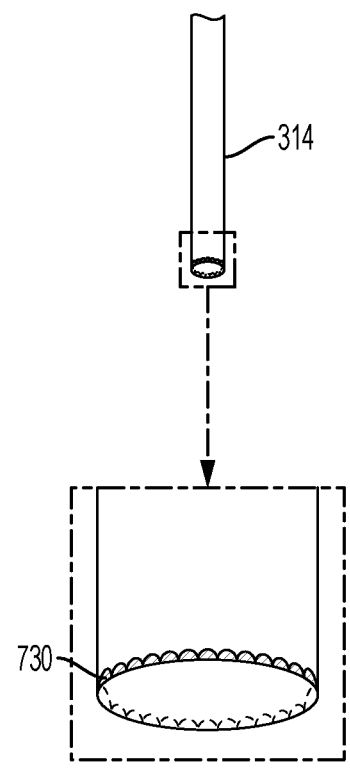

The tips the needles 314 may be structured to facilitate a degree of penetration into the minced skin particles 410. FIGS. 7A-7C show possible structures for such effect. In a general aspect, the tips may be sharp in order to penetrate the minced skin particles 410. For example, the thickness of the needle wall that defines the hollow bore (lumen) of a needle 314 may decrease toward the needle tip, such that the opening of the hollow bore at the needle tip is sharp along the rim of the opening. Referring to FIG. 7A, the thickness of the needle wall at a tip portion 710 of the needle 314 may decrease in approaching toward the rim of the opening.

Referring to FIG. 7B, the tips of the needle 314 may, instead of or in addition to the decreasing thickness mentioned above, have a serrated rim with protrusions 720 resembling fish teeth. The length of the protrusions (or teeth) may be less than the entire thickness of the minced skin particles, so as to penetrate only a partial thickness of the minced skin particles 410. Accordingly, leakage of suction pressure at the tip of the needle 314 can be minimized. For example, the length of the protrusions (or teeth) may be about 0.1 mm, and the (entire) thickness of the minced skin particles may be in a range of from about 0.15 mm to about 0.5 mm.

FIG. 7C shows another possible tip structure. Instead of the thickness of the needle wall decreasing evenly around the rim of the opening as in the case of FIG. 7A, the thickness of the needle wall may progressively decrease in approaching toward the rim only at partial portions 730 along the needle tip (the portions of the tip not marked by 730 have a constant thickness). In other words, the rim portion of the opening is partially sharp, alternating between a sharp section with a decreased thickness and a section with normal or less-decreased thickness. Therefore, the needle tip is strong and durable for multiple use, while maintaining sharpness.

The rim of the opening of the hollow bore may be flat against (parallel to) the surface of the minced skin particle 410 when the rim touches the minced skin particle 410, such that the rim of the opening contacts the minced skin particle evenly along the entire rim. Accordingly, when suction is applied by the vacuum pump 332, pressure loss at the opening can be minimized, and the minced skin particle 410 can be effectively attached to the opening of the needle 314. Furthermore, as illustrated in FIG. 6B, in order for the rim of the opening of the needle 314 to contact the minced skin particles 410 evenly, the rim may be at a certain angle (relative to the longitudinal axis of the needle 314 when the needle is straight) to account for the angle at which the needle 314 approaches the minced skin particle 410. The angle of the opening may vary among the needles 314 of the needle array 313, to account for differences in the angle of approach.

When the needles 314 have flexible intermediate sections 314a but also have other sections that lack the flexibility to traverse the bend 322c, the needle guide array 320 may have a separable structure in which upper body portion 326 (along with the sections of guide channels 322 therein) is separable from lower body portion 328 (along with the sections of guide channels 322 therein), to facility the insertion of the needles 314. For example, the needles 314 can be first inserted into the upper body portion 326 without the lower body portion 328 attached. Afterwards, the needles 314 can then be bent for insertion into the angled sections of guide channels 322 in the lower body portion 328.

One skilled in the art would appreciate that the needles 314 may be made of any materials suitable for the operations discussed in this disclosure. For example, surgical grade plastics and/or materials used in needles/catheters designed for percutanous transluminal coronary angioplasty may be used for the intermediate section 314a or other sections (when flexible). Surgical grade metal may be used for sections not required to be flexible, such as lower section 314b or the tip portion of the lower section 314b.

The needles 314 may have respective lengths such that, when inserted through the needle array guide 320 for contact with the minced skin graft 106a, the tips of the needles 314 all reach a respective minced skin particle 410 in an effective manner. For example, if the minced skin graft 106a is laid on a flat surface, the needles 314 may extend such that the vertical distances between their tips and the lower surface of the needle array guide 320 is uniform for all or substantially all of the needles 314 when they touch the minced skin graft 106a.

When the needles 314 converge to the minced skin particles 410 located at a central region, as in the illustrated case of FIGS. 5A-5B, the needles 314 on the outer periphery travel a greater distance than those at the center through the angled portions of the guide channels 322 and then through the distance from the openings 324 to the minced skin particles 410. Since the needles 314 may be attached to platform 312, the needles 314 may move together when the skin graft expansion apparatus 110 is operated; therefore, in order for all or substantially all of the needles 314 of the needle array 313 to reach the respective minced skin particles 410 substantially simultaneously when the minced skin particles 410 are on a planar surface, the needles 314 along the outer periphery of the needle array apparatus 310 may have a length that is longer than those toward the center of the array. For example, when there is a large array of needles 314 and corresponding guide channels 322 (such as larger than a 3×3 array), the needles 314 may be progressively longer from a central position to the peripheral positions.

The needle array 313, the collective arrangement of the guide channels 322, and the openings 324 may be in any suitable geometric form or arrangement, so as long the needles 314 of the needle array 313 are able to effectively fit into and through the guide channels 322. FIGS. 3A-3C, 8A-8B, and 9A show example embodiments having two-dimensional rectangular arrays in which the needles 314, guide channels 322, and openings 324, arranged in plural rows and plural columns, but the disclosure is not limited thereto. In general, the needles 314, the guide channels 322, and the openings 324 of the guide channels 322, may be arranged in an array of any overall form; such array may be one-dimensional arrangements or two-dimensional arrangements of the foregoing elements (the needles 314, guide channels 322, and/or the openings 324). One-dimensional arrangements include a single row of the foregoing elements (i.e., the needles 314, guide channels 322 and/or the openings 324 arrayed in a single line). Two-dimensional arrangements include rectangular (including square), round, oval, irregular, and other forms. In two-dimensional arrangements, the foregoing elements (the needles 314, guide channels 322, and/or the openings 324) may be generally arranged in plural rows (having the same or different number of elements) and plural columns (having the same or different number of elements). Therefore, depending on geometric form or arrangement of these features, the tips of the needles 314, upon passing through and exiting the needle array guide 320, may be arrayed in linear, rectangular, round, oval, irregular, and other forms when approaching the minced skin particles 410. In one possible implementation, the openings 324 of the guide channels 322 may have an overall shape that is similar to the shape of the open wound to be treated by the skin grafting.

As a possible further feature of the needles 314, the needles 314 may have surface properties as follows. The dermal layer of skin is hydrophilic, while the epidermal layer of skin is hydrophobic. Because the dermal side of a minced skin particle 410 readily attaches to hydrophilic materials, needles 314, which are used to pick up the minced skin particles may be coated with a hydrophilic coating. As a result, the needles 314 can more easily pick up minced skin particles. The hydrophilic coating may be applied to at least a tip portion of the needles 314.

As a possible further feature of the needle array guide 320, an area around the openings 324 contacted by the minced skin particles 410 (such as the bottom 323 of the needle array guide 320 around the openings 324) may be coated with a hydrophobic coating or be made of a hydrophobic material, in order to facilitate detachment of minced skin particles the openings 324 on the bottom of the needle array guide 320. Additionally, because static electricity may occur on the minced skin particles, a hydrophobic property would also cause the static electricity to be removed from the bottom of the needle array guide 320.

Figure 8A:
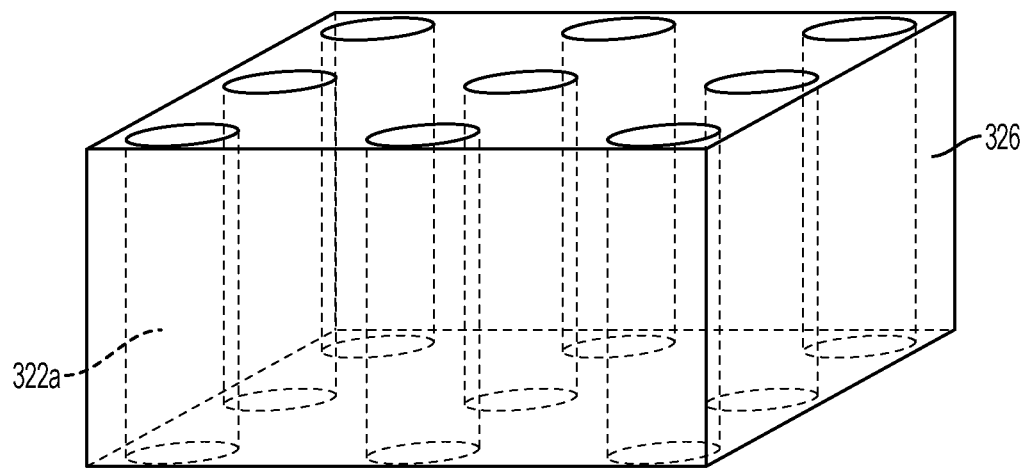
FIGS. 8A-8B respectively illustrate upper and lower portions of the needle array guide.
Figure 8B:
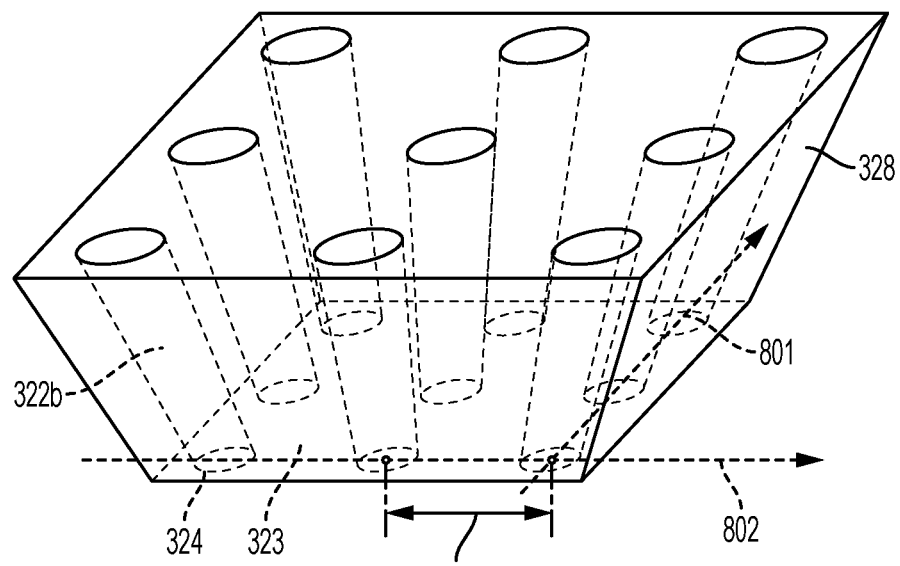

FIGS. 8A-8B respectively illustrate the upper body portion 326 and the lower body portion 328 of the needle array guide 320. 322a denotes the sections of the guide channels 322 located in the upper body portion 326, and 322b denotes the sections of the guide channels 322 located in the lower body portion 328. The bottom-side openings of sections 322a align with the top-side openings of sections 322b when the upper body portion 326 and the lower body portion 328 are brought together.

The openings 324 on the bottom 323 of the needle array guide 320 may have, along one or both of directions 801 and 802, any suitable center-to-center distance, labeled as distance s in FIG. 8B. The center-to-center distance may be, for example, in a range of from about 4 mm to about 7 mm, or from about 5 mm to about 6 mm. The opening 324 may each have a diameter in a range of from about 0.4 mm to about 0.6 mm, or from about 0.45 mm to about 0.55 mm, such as about 0.5 mm. However, one skilled in the art would appreciate that these dimension are for proposes of example only, and that other dimensions may also be suitable. Moreover, it is noted that the openings 324 and the channels 322a, 322b have been illustrated in FIGS. 8A-8B for simplicity and clarity and have not necessarily been drawn to scale.

Figure 9A:
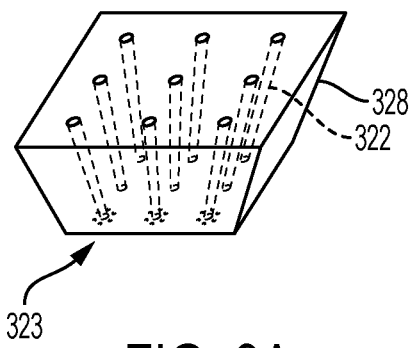
FIG. 9A-9C illustrate a configuration of the needle array guide according to one or more embodiments of the present disclosure.
Figure 9B:
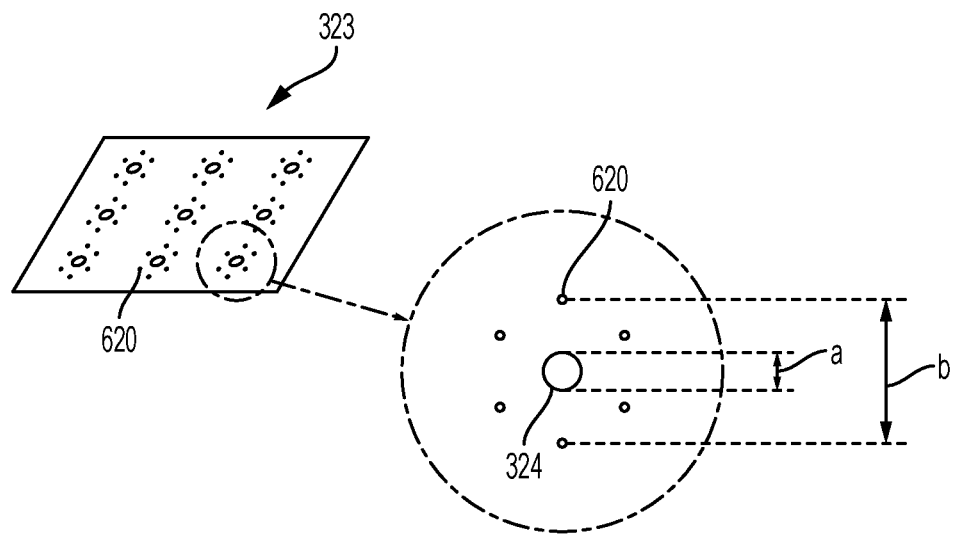
Figure 9C:
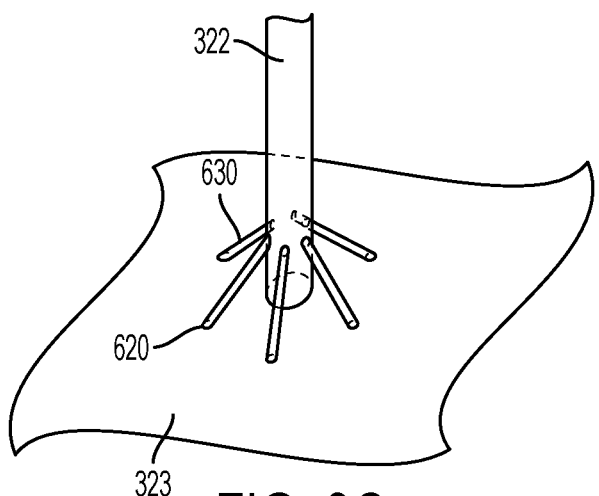

FIGS. 9A-9C illustrate yet another possible further feature of the needle array guide 320. After the needles 314 have been retracted into the openings 324, the minced skin particles 410 may adhere to the area around the openings 324 on the bottom 323 of the needle array guide. To facilitate detachment of the minced skin particles 410, air holes 620, which connect to the guide channels 322 through air hole channels 630, may be provided on the bottom 323 of the needle array guide 320. Therefore, when the needle 314 is pulled into the channels and positive air pressure is applied, the air is expelled through the air holes 620. In this way, the minced skin particles 410 can detach from the bottom 323 of the needle array guide 320.

The air holes 620, which connect to the guide channels 322, may be disposed so as to surrounding each opening 324 on the bottom 323 of the needle array guide. The distance between the air holes 620 and the distance between opening 324 and air holes 620 may be less than half of the diameter of the minced skin particles. For example, if the diameter of the microskin graft is 1 mm and the diameter a of the opening 324 is 0.5 mm, the distance between the air holes 620 and the center opening 324 may be 0.5 mm. For a circle (outside the opening 324) that has a diameter b of 1 mm (for a radius of 0.5 mm), the circumference of the circle would be 3.14 mm based on the equation: diameter=$2\pi r$. As a result, there may be 6 air holes 620 positioned along the circle with the diameter of 1 mm.

The diameter of the air holes 620 may be about 0.1 mm. The opening 324 may have a diameter in a range of about 0.45 mm to about 0.55 mm, as noted above, and the number of air holes 620 may be six air holes arranged at a distance of about 0.5 mm or less from the center of the opening 324. The distance may be within a range of about 0.1 mm to about 0.5 mm. However, one skilled in the art would appreciate that these dimension are for proposes of example only, and that other dimensions may also be suitable.

Figure 10:
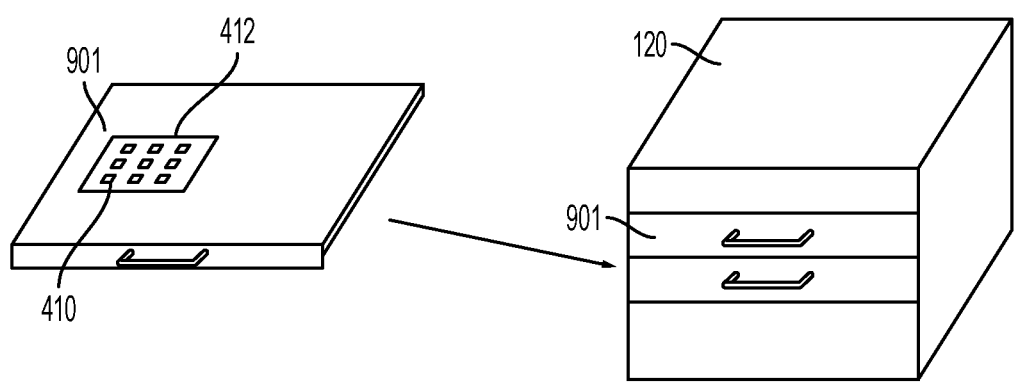
FIG. 10 illustrates a moist chamber according to one or more embodiments of the present disclosure.

FIG. 10 illustrates a moist chamber. The moist chamber may include multiple drawers 901 having a plurality of tiny holes (perforations). Normal saline or water is kept on the bottom of the chamber. The humidity is higher than surrounding environment. The expanded minced skin particles 410 and the carrier 412 may be kept in the moist chamber is prevented from dry in the chamber while it is waiting for transfer to wound bed.

The skin grafting system may include any structure suitable to perform physical manipulations, such as the movement and positioning of the skin graft cutter 101 and/or the cutting board 104, the movement and positioning of the skin graft expansion apparatus 110, the operation of moving the needle array apparatus 310 relative to the needle array guide 320 for the needles 314 to be protruded out of and retracted back into the openings 324, and any other physical manipulations in connection with the operations of various components discussed in this disclosure. Such suitable structures may include robotic components used in robotically-implemented surgical systems. For example, actuator 340 shown in FIG. 3B may be used to move the needle array apparatus 310 (and hence the needle array 313) relative to the needle array guide 320, to thereby adjust the separation distance between the platform 312 and the needle array guide 320.

Figure 11:
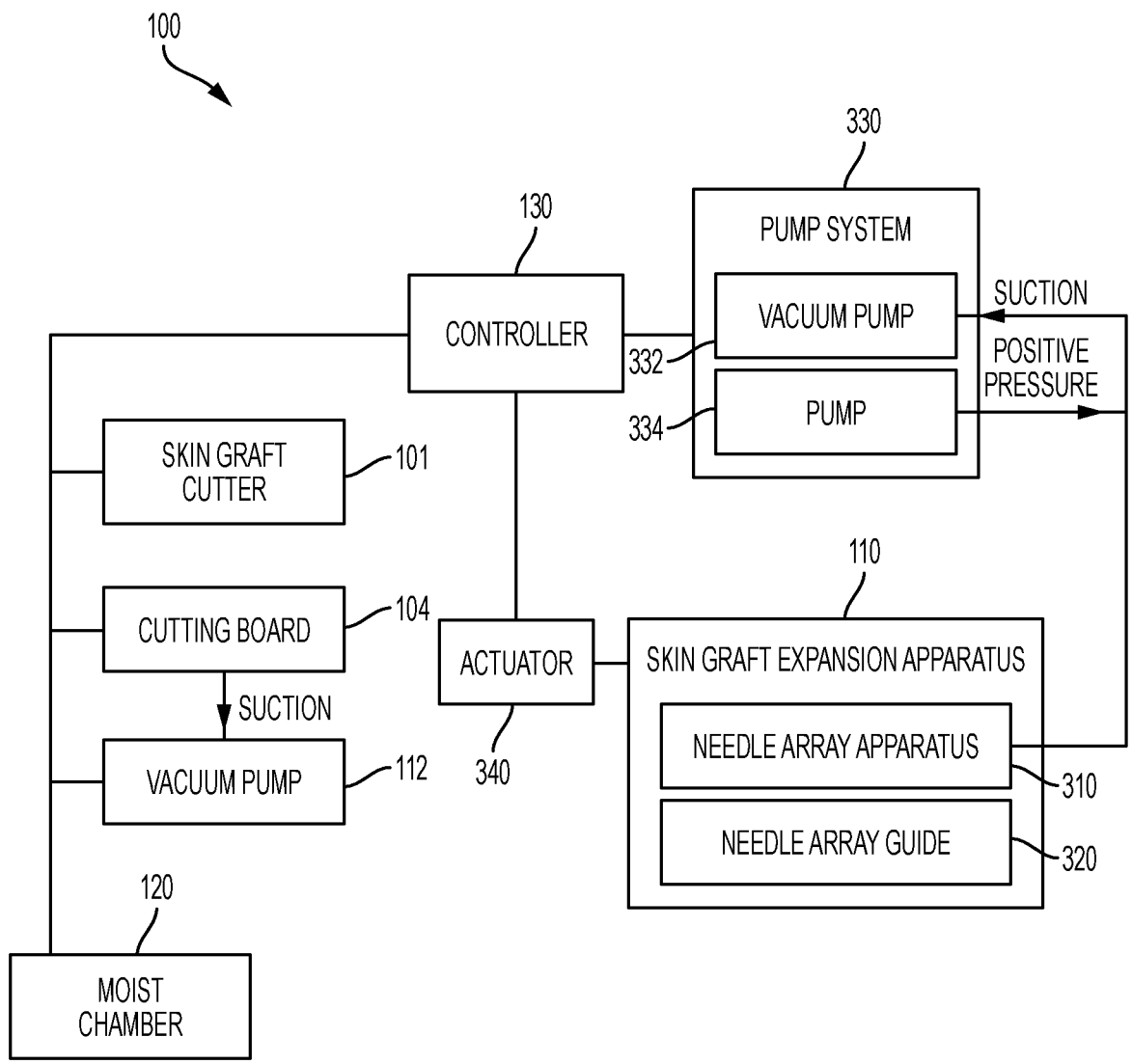
FIG. 11 is a block diagram of the skin grafting system.

FIG. 11 is a block diagram of the skin grafting system 100. As illustrated, the system 100 may include a controller 130 that controls the operations of various components in the system 100. The controller 130 may comprise at least one hardware processor, such as a computer processor, configured or programmed to control the system to perform the operations discussed above. The controller 130 may cause the performance of the operations by controlling structures (such as actuator 340) configured to carry out the aforementioned physical manipulations. In particular, the controller 130 may be configured to control the actuator 340 to adjust the separation distance between the platform 312 and the needle array guide 320 such that the needles protrude out of the openings 324 to an appropriate distance d (see FIGS. 5A-B) between the bottom 323 of the needle array guide 320 and the minced skin particles 104.

The controller 130 may also be configured to control the vacuum pump 112 and the pump system 330. The controller 130 may carry out the control functions based on or in response to inputs or commands from a surgeon or other operator of the system. The controller 130 may be configured to repeatedly perform the skin particles transportation process to transport the multiple groups of minced skin particles onto the carrier.

The at least one hardware processor of controller 130 may be programmed to perform any or all of the functions mentioned in this disclosure by program/software recorded on a non-transitory computer-readable storage medium, which may be any data storage device that can store data which can be thereafter read by a computer system. In other words, the non-transitory computer-readable storage medium may store the program/software, which, when executed by the at least one hardware processor, causes the controller 130 to control the system 100 and/or the skin graft expansion apparatus to perform the functions and methods discussed in this disclosure. The program/software implementing the embodiments may also be transmitted over transmission communication media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

In the skin grafting system 100, the vacuum pump 112 and the vacuum pump 332 may be implemented as separate vacuum pumps, but may also be implemented as the same vacuum pump, in which case, the vacuum pump 332 of pump system 330 may perform the functions of vacuum pump 112.

The combination of the skin graft expansion apparatus 110 and the actuator 340 may be referred to as a skin graft expansion device. Such skin graft expansion device may include further components such as the controller 130 and/or pump system 330.

Hereinafter, a method of transporting tissue from a donor skin graft to a carrier will be described. The method includes cutting skin graft to obtain minced skin particles and expanding the minced skin graft.

The process of cutting skin graft may be performed as follows, with reference to the features of the skin grafting system 100 discussed above. After an appropriately sized area of donor skin 106 has been obtained (such as by a harvesting procedure), the donor skin 106 is transferred to cutting board 104, which may have been sterilized beforehand. The donor skin 106 may be placed on the cutting board 104 with the dermal side up. In one possible implementation, vacuum-pressure may be used to hold the donor skin 106 in place. For example, the controller 130 may control vacuum pump 112 to exert a vacuum pressure inward from the holes 108 of the cutting board, in order to hold the harvested donor skin 106 on the cutting board and to keep the donor skin 106 flat before and after the cutting.

The skin graft cutter 101 is operated such that the parallel blades 102 (or other cutting apparatus) of the skin graft cutter 101 cut through the donor skin 106, thereby cutting the donor skin into stripes of a desired width in the manner shown in FIG. 2. After the first cut, the parallel blades 102 or cutting board 104 are rotated relative to each other by a certain angle, such as an angle of about 90°. For example, the controller 130 may control the rotation of either the parallel blades 102 or the cutting board 104 alone, or rotate both of them, in order to achieve the relative rotation. After the rotation, parallel blades 102 are operated to cut the donor skin 106 a second time. In this manner, the donor skin is cut into minced skin graft 106a comprising minced skin (microskin) particles 410 of a desired size. The minced skin particles 410 are kept in situ by vacuum pump 112, which is still being controlled to apply the vacuum pressure through the holes 108. Alternatively or additionally, a metal chamber (not shown) with stripe windows can also be used to keep skin particles in place. Then, the blades 102 are removed from the minced donor skin 106a.

The size of the minced skin particles 410 may be about 1×1 mm or below 1×1 mm. For example, the size may be in a range of about 0.8×0.8 mm to about 1×1 mm.

The minced skin particles skin 410 may be oriented with the dermal side facing up and epidermal side facing down, but it is not necessary for the skin to be in this orientation for attachment to the needles 313, even the needles 313 are coated with a hydrophilic coating.

The process of expanding the skin graft to a desired expansion ratio may comprise: converging the tips of the needles 314 of the needle array 313 closer toward one another; bringing the tips of the needles 314 into contact with the minced skin particles 410 (which may occur concurrently with the converging of the tips closer toward one another); attaching the tips of the needles 314 to the minced skin particles; retracting and separating apart the tips of the needles 314; and depositing the minced skin particles onto a carrier 412. In greater detail, this process may be performed as follows. The skin graft expansion apparatus 110 (particularly, the needle array guide 320) is operated so as to be positioned above the minced skin particles 410. Referring to FIGS. 3A-3C, 4A-4C, and 6A-6C, the needles 314 of the needle array apparatus 310 are moved through the needle array guide 320 by adjusting the distance between the platform 312 and the needle array guide 320, such that the needles 314 pass through the guide channels 322 of the needle array guide 320. By passing through the needle array guide 320, the needles 314 are guided in a convergent manner such that the tips of the needles 314 converge toward the minced skin particles 410 to permit attachment of the minced skin particles 410 to the needles 314. Attachment can be effectuated or assisted by the vacuum pressure of pump system 330, which may be controlled by the controller 130. The controller 130 may also control the operations of positioning the skin graft expansion apparatus 110 above the minced skin particles 410, and the operations of passing the needles 314 through and out of the bottom of the needle array guide 320, and retracting the needles back into the needle array guide 320.

After the minced skin particles 410 have been held tightly by each needle with the assistance of the vacuum pressure from vacuum pump system 330, the needle array apparatus 310 and the needle array guide 320 are separated apart from each other so that the tips of the needles 314 are retracted into the guide channels 322 of the needle array guide. The retraction causes the tips of the needles 314 to diverge (separate with respect to each other). When the needles 314 are retracted inside the channels 322, the minced skin particles 410 become held on the holes 324 on the bottom of the needle array guide 320 with the assistance of the vacuum suction applied through the needles 314. The minced skin particles 410 have now been spaced apart from each other, in accordance with the expansion ratio of the operation.

Then, the needle array guide 320 with skin grafts is moved away from cutting board 104 and to carrier 412 used to transfer grafts to wound bed. As a result of the graft skin expansion apparatus 110, the minced skin particles are loaded on the carrier 412 with desired expansion ratio when the vacuum pressure is released and a positive air pressure is applied by the pump system 330. Thus the graft, comprising the expanded minced skin particles 410, is ready to be transfer to wound bed or to a moist chamber.

The method may be performed entirely by the controller 130, which may thus be configured to perform any of the operations discussed above. Alternatively, some or all of the operations may be performed manually (instead of automatically by the controller 130).

The method may further include an operation of transporting the graft and the carrier 412 into a moist chamber 120 that contains normal saline or water on the bottom. The method may further include spraying the graft with normal saline to prevent dry while it is waiting for transplantation. The transporting of the graft into the moist chamber 120 and the spraying can be performed mechanically, under control of the controller 130, or manually.

The process of cutting the skin graft may result in more minced skin particles 410 than the number of the minced skin particles 410 that can be expanded in one iteration of the process of expanding the skin graft (in which case, the "minced skin particles 410" discussed in the process of expanding the skin graft refers to only a portion of all minced skin particles 410 obtained in the process of cutting the skin graft). Thus, the operations of positioning the needle array guide 320 above minced skin particles 410, expanding the minced skin particles 410, and releasing the expanded minced skin particles 410 onto the carrier 412, may be a sequence that is repeated multiple times until all minced skin particles 410 have been transported to the carrier. For example, if the donor skin graft 106 was cut into 1200 minced skin particles 410 by the skin graft cutter 101 and the needle array 313 has 100 needles, the above process may be repeated 12 times.

The method discussed above may be included as part of a skin grafting method that includes: harvesting the donor skin 106; performing the above mentioned method of transporting tissue from a donor skin graft to a carrier; and transferring the expanded minced skin particles 410 and the carrier 412 to a wound.

The needle array guide 320, skin graft expansion apparatus 110, the skin grafting system 100, and method of transporting tissue from a donor skin graft to a carrier may be embodied so as to obtain the benefits discussed below.

The needle array guide 320, skin graft expansion apparatus 110, skin grafting system 100, and method of this disclosure permit the donor site to be small. The maximum skin expansion ratio for the Tanner mesh technique is 1:6, while the maximum ratio for MEEK graft is 1:9. However, embodiments of the present disclosure can obtain an expansion ratio of 1:100 when the donor skin is cut into 0.8 mm×0.8 mm. For better understanding, suppose a patient with severe deep burn injury with 100% TBSA (Total Body Surface Area). 1% TBSA is equal to the size of one of this patient's hands. Therefore, harvesting donor skin of an area as little as the size of the patient's hand would be sufficient to repair the burn wound by microskin grafting. However, 16.7 times (nearly a person's entire back) and 11.1 times (nearly an arm of a person) the size of donor graft would be needed to repair the same wound by using Mesh grafting and MEEK grafting, respectively. A donor site injury about the size of a person's hand is comparable to that of the CEA technique, which needs to harvest 5 cm² skin tissue for cell culture.

The skin graft expansion apparatus 110, skin grafting system 100, and method of this disclosure permit the donor skin to be quickly transported onto a carrier. Labor intensity and time consumption are obstacles to widespread application of microskin grafting. When microskin grafting with an expansion ratio of 1:9 is used to repair a 50% TBSA burn wound, over 113,000 microskin grafts would be needed, as well as over 28 hours to prepare the donor graft (moving a single needle 4000 times per hour would require 113,000/4000=28.25 hours to move 113,000 skin particles). It is unsafe for patient to stay in operation room for such a long time. Importantly, the survival rate of microskin graft is significantly limited when there is no blood supply to skin graft for such a long time.

The needle array guide 320, skin graft expansion apparatus 110, skin grafting system 100, and method of this disclosure permit the speed of transporting tissue from donor skin to a carrier to raised according to the number of arrayed needles in the needle array 313. The array can be designed as 5×5, 10×10, 20×20, etc. By using a relatively large array, a high speed can be realized. For example, by using robotically implemented method, a time of 67.2, 16.7 or 4.2 minutes for transferring 113,000 skin particles is attainable by a 5×5, 10×10, and 20×20 needle array, respectively. As noted above, the most important reason for low viability of cells in microskin graft over time is the lack of blood supply for harvested graft, which, in conjunction with the small tissue volume of microskin grafts, results in the tissue drying quickly in air. The high speed of transporting skin tissue attainable by embodiments of this disclosure enables most of cells to be transplanted to a wound in a quite short time, while they remain viable.

When transporting large amounts of minced skin particles 410 (on the order of several hundreds to tens of thousands), a robotic implementation of the skin graft expansion apparatus of this disclosure can perform the transporting process at a rate that is n times faster than a robotically implemented transporter configured to transport only one skin at a time, where n is the number of needles in the needle array (i.e., n=25, 100 and 400 for a 5×5, 10×10, and 20×20 needle array, respectively).

Furthermore, the skin graft expansion apparatus, skin grafting system, and method of this disclosure permit skin grafting to be performed safely, without the need of chemicals in the grafting process. On the other hand, MEEK graft, for example, uses a glue which does not need to be sterilized in the skin graft process. This was a reason why the MEEK technique was approved rather late in the U.S. after it had been developed. CEA, for example, requires the use of mouse cells and a cell culture medium that contains animal serum in cell culture.

Furthermore, while the MEEK technique requires harvesting a very thin donor skin less than 0.15 mm thickness, the skin graft expansion apparatus, skin grafting system, and method of this disclosure are not limited to a certain thickness of the microskin.

Furthermore, the skin graft expansion apparatus, skin grafting system, and method of this disclosure may use donor skin tissue available at any level of hospitals. The skin graft expansion apparatus can be used repetitively. The carrier 412 for the graft can be used one time, but can be an ordinary gauze, which is readily available. Compared to CEA, the skin graft expansion apparatus, skin grafting system and method of the present disclosure can be implemented at a much lower cost, without requirement of an expensive laboratory for cell culture.

Inclusion in this disclosure of any characterization of any product or method of the related art does not imply or admit that such characterization was known in the prior art at the time a claimed invention was made, even if the product or method itself was known in the prior art at the time. For example, if a related art document discussed in this disclosure constitutes prior art, the inclusion of any characterization of the related art document does not imply or admit that such characterization of the related art document was known in the prior art or would have been appreciated by one of ordinary skill in the art at the time a claimed invention was made, especially if the characterization is not disclosed in the related art document itself.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A needle array guide for a skin graft expansion apparatus, the needle array guide comprising:
   a body portion including an upper body portion and a lower body portion, the lower body portion including openings; and
   guide channels located in the upper body portion and in the lower body portion,
      the guide channels in the upper body portion are substantially parallel to each other and the guide channels located in the lower body portion are respectively angled in a convergent manner to lead to the openings and converge closer toward one another as the guide channels in the lower body portion approach the openings,
      the guide channels receiving a plurality of hollow needles, the plurality of hollow needles are arranged in a needle array and having respective tips configured to be attachable to minced skin particles obtained from a skin graft, the guide channels in the lower body portion to guide movement of the plurality of hollow needles when the plurality of hollow needles are configured to be protruded from the openings toward the minced skin particles and when the plurality of hollow needles are configured to be retracted toward the openings.

2. The needle array guide according to claim 1, the lower body portion having a bottom surface on which the openings are disposed.

3. The needle array guide according to claim 1, wherein the body portion has a tapered shape.

4. The needle array guide according to claim 3, wherein the tapered shape is a frusto-pyramidal shape.

5. The needle array guide to claim 1, wherein
   the guide channels have respective lower sections located in the lower body portion, and respective upper sections located in the upper body portion.

6. The needle array guide according to claim 1, wherein the openings include at least three openings.

7. The needle array guide according to claim 1, wherein the openings include 9 openings arranged in a 3×3 array.

8. A skin graft expansion apparatus comprising:
a needle array guide including an upper body portion, a lower body portion, and guide channels located in the upper body portion and in the lower body portion,
the guide channels located in the upper body portion are substantially parallel to each other and the guide channels located in the lower body portion are respectively angled in a convergent manner to lead to openings in the lower body portion and, converge closer toward one another as the guide channels in the lower body portion approach the openings; and
a needle array apparatus including a platform and a needle array including a plurality of hollow needles attached to the platform,
the plurality of hollow needles having respective tips configured to be attachable to minced skin particles obtained from a skin graft,
the plurality of hollow needles to be received in the guide channels so as to be guided by the guide channels when moving relative to the needle array guide, and
the tips of the plurality of hollow needles are configured to be protrudable out of the openings toward the minced skin particles and retractable into the openings.

9. The apparatus according to claim 8, wherein
the guide channels have respective lower sections located in the lower body portion, and respective upper sections located in the upper body portion,
a plurality of the lower sections are angled in the convergent manner, and
a portion of each hollow needle of the plurality of hollow needles have a flexible intermediate section, to allow the portion of the hollow needles to bend when transitioning from an upper section of the upper sections of the guide channels to a lower section of the lower sections of the guide channels.

10. The apparatus according to claim 8, wherein
tip portions of the plurality of needles are coated with a hydrophilic coating, and
areas of the needle array guide around the openings are coated with a hydrophobic coating.

11. A skin grafting system comprising:
the skin graft expansion apparatus according to claim 8; and
a pump system connected to the plurality of hollow needles to vacuum an interior of the plurality of hollow needles to thereby cause the tips of the plurality of hollow needles to be configured to be attachable to the minced skin particles by vacuum suction, and to apply positive pressure to the plurality of hollow needles.

12. The system according to claim 11, wherein, when the plurality of needles are retracted into the openings after tips of plurality of hollow needles have attached to the minced skin particles, the pump system applies a vacuum to the guide channels through the plurality of hollow needles, to thereby hold the minced skin particles on the openings.

13. The system according to claim 11, wherein the pump system is to apply the positive pressure to be configured in detaching the minced skin particles from the openings.

14. The system according to claim 13, wherein
the openings are disposed on a bottom surface of the needle array guide, and
the bottom surface of the needle array guide includes a plurality of air holes positioned around an opening corresponding to a guide channel among the guide channels,
so that when the pump system applies the positive pressure to detach the minced skin particles from the openings, the positive pressure is applied out of both the opening corresponding to the at least one of the guide channel among the guide channels and the plurality of air holes.

15. A skin grafting system comprising:
the skin graft expansion apparatus according to claim 8; and
an actuator to move the plurality of hollow needles relative to the plurality of guide channels, to thereby move the plurality of hollow needles out of the openings and retract the plurality of hollow needles into the openings.

16. A skin grafting system comprising:
the skin graft expansion apparatus according to claim 8;
a pump system connected to the plurality of hollow needles, to vacuum an interior of the plurality of hollow needles to thereby cause the tips of the plurality of hollow needles to be configured to be attachable to the minced skin particles by vacuum suction, and to apply positive pressure to the plurality of hollow needles; and
a controller comprising at least one hardware processor to control the skin graft expansion apparatus to perform a skin particles transportation process comprising:
operating the skin graft expansion apparatus to protrude the plurality of hollow needles out of the openings by increasing a distance between the platform and the needle array guide, such that the tips of the plurality of hollow needles converge closer toward one another to be configured to come into contact with the plurality of minced skin particles,
causing the minced skin particles to attach to the tips of the plurality of hollow needles by operating the pump system to generate the vacuum suction,
while maintaining the vacuum suction, retracting the plurality of hollow needles back into the openings by decreasing the distance between the platform and the needle array guide, to cause the minced skin particles to separate apart and cause the minced skin particles to attach to the openings, and
operating the pump system to release the vacuum suction and apply positive pressure to the plurality of hollow needles, to cause the expanded minced skin particles detach from the openings and the expanded minced skin particles be deposited onto a carrier.

17. The system according to claim 16, wherein the at least one hardware processor is to control repeatedly performing of the skin particles transportation process to transport multiple groups of minced skin particles onto the carrier.

18. The system according to claim 16, further comprising:
a cutting board configured to receive a donor skin graft;
a skin graft cutter configured to perform a cutting operation of cutting the donor skin graft into the minced skin particles; and
wherein the controller is to control the skin graft cutter to perform the cutting operation.

19. The system according to claim 18, wherein
the cutting board comprises a plurality of holes on a surface of the cutting board, and
the system further comprises a vacuum pump connected to the plurality of holes and to apply a vacuum suction to the plurality of holes to be configured in holding the donor skin graft on the cutting board.

20. A method of transporting tissue from a donor skin graft to a carrier performed by a controller, of a skin grafting system, that includes at least one hardware processor, the method comprising:

cutting a donor skin graft into minced skin particles;

picking up and expanding a plurality of the minced skin particles, by using a skin graft expansion apparatus of the skin grafting system, wherein the skin graft expansion apparatus includes:

a needle array guide including an upper body portion, a lower body portion and guide channels located in the upper body portion and the lower body portion, the guide channels located in the upper body portion are substantially parallel to each other and the guide channels located in the lower body portion are respectively angled in a convergent manner to lead to openings in the lower body portion and converge closer toward one another as the guide channels in the lower body portion approach the openings; and a needle array apparatus including a platform and a needle array including a plurality of hollow needles attached to the platform, the plurality of hollow needles having respective tips to be attachable to the minced skin particles, and the plurality of hollow needles being received in the guide channels so as to be guided by the guide channels when moving relative to the needle array guide, and the picking up and expanding the plurality of the minced skin particles includes:

increasing a distance between the platform and the needle array guide to protrude the tips of the plurality of hollow needles toward the minced skin particles, such that the tips of the plurality of hollow needles converge closer toward one another and come into contact with the plurality of minced skin particles;

attaching the minced skin particles to the tips of the plurality of needles; and retracting the plurality of hollow needles by decreasing a distance between the platform and the needle array guide, to thereby separate apart the minced skin particles; and placing the expanded minced skin particles onto the carrier.

21. The method according to claim 20, wherein the attaching the minced skin particles to the tips of the plurality of needles includes:

applying a vacuum suction to the plurality of hollow needles, to thereby facilitate attachment the plurality of minced skin particles to the tips of the plurality of hollow needles; and the retracting the plurality of hollow needles includes:

while maintaining the vacuum suction, retracting the plurality of hollow needles back into the openings, to thereby separate apart the minced skin particles and cause the minced skin particles to attach to the openings, and the placing the expanded minced skin particles onto the carrier includes:

releasing the vacuum and applying positive pressure to the plurality of hollow needles, to thereby detach the expanded minced skin particles from the openings and deposit the expanded minced skin particles onto the carrier.

22. The method according to claim 20, wherein the picking up and expanding the plurality of the minced skin particles expands the minced skin particles at an expansion ratio in a range of 1:10 to 1:100.

23. A needle array apparatus for a skin graft expansion apparatus, the needle array apparatus comprising:

a platform connectable to a vacuum pump; and a needle array including a plurality of hollow needles attached to the platform, the plurality of hollow needles having respective tips configurable to be attachable to minced skin particles obtained from a skin graft, a portion of each hollow needle of the plurality of hollow needles having a flexible intermediate section to allow the portion of the plurality of hollow needles to bend so as to converge closer to one another at a tip end of the needle array.

24. A skin grafting system, comprising:

the skin graft expansion apparatus according to claim 8, and a cutting board including:

a surface configurable on which to place a donor skin graft to cut the donor skin graft into the minced skin particles; and a plurality of holes on the surface.

25. The skin grafting system according to claim 24 further comprising:

a vacuum pump connected to the plurality of holes and to apply a vacuum suction to the plurality of holes to be configured to hold the donor skin graft on the cutting board.

* * * * *